United States Patent
Borrelli

(10) Patent No.: US 7,595,386 B2
(45) Date of Patent: Sep. 29, 2009

(54) METHODS AND COMPOSITIONS FOR HEAT ACTIVATED GENE THERAPY USING CYTOLETHAL DISTENDING TOXIN

(75) Inventor: Michael J. Borrelli, Troy, MI (US)

(73) Assignee: William Beaumont Hospital, Royal Oak, MI (US)

( * ) Notice: Subject to any disclaimer, the term of this patent is extended or adjusted under 35 U.S.C. 154(b) by 312 days.

(21) Appl. No.: 10/764,316

(22) Filed: Jan. 23, 2004

(65) Prior Publication Data

US 2006/0127359 A1  Jun. 15, 2006

Related U.S. Application Data

(60) Provisional application No. 60/442,473, filed on Jan. 24, 2003.

(51) Int. Cl.
*C07H 21/04* (2006.01)
(52) U.S. Cl. .............. 536/24.5; 536/24.31; 435/6; 435/325; 435/375
(58) Field of Classification Search ............ None
See application file for complete search history.

(56) References Cited

U.S. PATENT DOCUMENTS

2005/0032726 A1* 2/2005 Li et al. .................. 514/44

OTHER PUBLICATIONS

Frisan et al. Cytolethal distending toxins and activation of DNA damage-dependent checkpoint responses. Int. J. Med. Microbiol. 2002, 291: 495-499.*
Sert et al. The bacterial cytolethal distending toxin (CDT) triggers a G2 cell cycle checkpoint in mammalina cells without preliminary induction of DNA strand breaks. Oncogene 1991, 18: 6296-6304.*
Xu et al. Strategies for Enzyme/Prodrug Cancer Therapy. Clinical Cancer Research, 2001, vol. 7: 3314-3324.*

* cited by examiner

*Primary Examiner*—Kimberly Chong
(74) *Attorney, Agent, or Firm*—Brinks Hofer Gilson & Lione

(57) ABSTRACT

The invention provides compositions and methods for gene therapy using cytolethal distending toxins (CDTs). In a preferred embodiment, a gene therapy vector according to the invention includes a gene encoding a B subunit of a CDT and an antisense oligonucleotide that inhibits a DNA repair mechanism. An inducible promoter is operably linked to the gene and oligonucleotide. Preferably, the promoter is strictly inducible by heat shock.

3 Claims, No Drawings

METHODS AND COMPOSITIONS FOR HEAT ACTIVATED GENE THERAPY USING CYTOLETHAL DISTENDING TOXIN

CROSS-REFERENCE TO RELATED APPLICATIONS

This application claims priority to U.S. Provisional Application No. 60/442,473 filed on Jan. 24, 2003, entitled "Methods and Compositions for Heat Activated Gene Therapy Using Cytolethal Distending Toxin."

FIELD OF THE INVENTION

The present invention relates to methods and compositions for conducting gene therapy. More particularly, the present invention relates to cytolethal gene therapy using toxins.

BACKGROUND OF THE INVENTION

Gene therapy holds great promise as a clinical treatment for a variety of human maladies. Gene therapy involves the delivery of an exogenous gene or other polynucleotide to a cell or plurality of cells. The exogenous gene carries the therapy in the sense that it is a composition that will, by way of its introduction into the cell, confer benefits onto the cell and/or host. The benefits conferred onto the cell are typically designed to be therapeutic to the host. Thus, the benefits are typically designed to correct a deficiency or to kill an undesirable cell.

Many different therapeutic strategies for gene therapy have been devised. In one approach, a natural gene that is defective for one reason or another is replaced with an exogenous copy of the gene that is more suitable for achieving the function and/or purpose of the gene. For example, a wild-type exongenous gene can be introduced as a replacement for a mutant, less effective natural gene. This approach holds promise for disease conditions in which an individual produces ineffective gene products, such as cystic fibrosis.

In another approach, a special gene, frequently referred to as a "suicide gene", is delivered to one or more cells of interest. The suicide gene encodes a gene product that is toxic to the cell. Accordingly, production of the suicide gene product ultimately leads to the death of the cell. This approach holds promise for treatment of disease conditions in which it is desirable to eliminate certain cells from a host, such as in various forms of cancer.

In both of these approaches, delivery of the exogenous gene to the cells of interest presents a challenge. Frequently, a vector of some type is used to deliver the gene to the cells or tissue being treated. For several reasons, viral vectors are currently the most frequently used vector in gene therapy procedures. The natural replication cycle of a virus enables the vector to reproduce its genetic contents, including any exogenous genes, using the molecular machinery of an infected cell. Subsequently, the infected cell releases the resultant daughter vectors to the surrounding environment. This allows the exogenous gene to be repeatedly introduced into new cells, thereby expanding the area in which the therapy occurs beyond the originally infected cell.

Some benefits of using a viral vector are lost, however, when a suicide gene is utilized. By nature, the suicide gene encodes a product that is toxic to the cell. Thus, the gene encodes a product that will ultimately kill the cell. If the suicide gene is sufficiently toxic, the cell may perish before the vector is able to replicate and repackage itself for delivery to other cells. As a result, the distribution of the therapy, i.e., the suicide gene, can be stopped prior to expansion beyond the original cells, which may decrease the effectiveness of the therapy.

Some toxins, such as the shiga, cholera, and diptheria toxins, appear to be sufficiently toxic to create this situation. Indeed, elaborate molecular "choke" mechanisms have been used to slow the production of the suicide gene product in order to allow production and packaging of viral components.

BRIEF SUMMARY OF THE INVENTION

In one aspect, the present invention provides gene therapy vectors that include one or more suicide gene and various control elements. The suicide gene is a gene for a cytolethal distending toxin (CDT), and is preferably a gene for a B subunit of a CDT. The control elements include an inducible promoter and an antisense oligonucleotide that inhibits expression of a nucleic acid that encodes a DNA repair protein. The inducible promoter is preferably a heat shock promoter, and particularly preferably a segment of a heat shock promoter that is strictly inducible by heat shock. The antisense oligonucleotide preferably inhibits expression of a DNA repair protein that functions to repair DNA damaged in a manner that reflects the type of damage induced by the suicide gene. Preferably, the antisense oligonucleotide inhibits expression of ku70, a protein that is critical to the functioning of the non-homologous end joining DNA repair mechanism. This inhibits repair of double-strand breaks in DNA, such as those induced by B subunits of CDTs.

The control elements ensure that the suicide gene is expressed only under certain conditions. This, in turn, provides an opportunity for the vector to replicate and repackage for delivery to additional cells prior to expression of the suicide gene. Also, the control elements prevent the cell from repairing damage induced by the suicide gene. Interestingly, the ku70 antisense control element also sensitizes the cell to other forms of DNA-damaging therapy, such as radio- and chemotherapy.

Thus, a preferred embodiment of a composition according to the present invention comprises a vector including a polynucleotide that has a first nucleotide sequence that encodes a B subunit of a CDT, second nucleotide that encodes an antisense oligonucleotide that inhibits expression of ku70, and a heat shock promoter that is strictly inducible by heat and that is positioned to promote expression of the first and second nucleotide sequences.

In another aspect, the present invention also provides methods of conducting gene therapy. The methods utilize a vector according to the present invention. Accordingly, the methods include steps directed at inducing the inducible promoter to drive expression of the suicide gene and the antisense oligonucleotide. As indicated above, the preferred embodiment of the vector according to the present invention includes a heat shock promoter as one of the control elements.

Appropriate steps for inducing the promoter, therefore, include elevating the temperature of the cell and/or tissue to which the vector has been delivered to a temperature above normal body temperature. Various hyperthermia techniques can be employed to accomplish this temperature elevation. Thus, a preferred method according to the present invention comprises delivering a vector according to the present invention to a tumor. Also, the method includes elevating the temperature of the tumor to a temperature that is sufficient to induce the promoter to express the suicide gene and the antisense oligonucleotide.

DETAILED DESCRIPTION OF THE INVENTION

The present invention provides methods and compositions for conducting gene therapy. The methods and compositions utilize cytolethal distending toxins, or subunits thereof. While the following description of preferred embodiments and methods provides examples of the present invention, the description is not intended to limit the scope of the invention in any manner. Rather, the description serves to enable a person of ordinary skill in the relevant art to practice the present invention.

1. Definitions

The following definitions apply for the indicated terms:

The term "gene therapy" is given its ordinary meaning in the art. Briefly, "gene therapy" refers to the transfer of genetic material (e.g., a DNA or RNA polynucleotide) of interest into a host cell and/or tissue to treat or prevent a disease condition. The genetic material of interest typically encodes a product whose in vivo production is desired. The genetic material of interest can also include various control elements, such as transcriptional promoters. In the present invention, the genetic material of interest includes a cytolethal distending toxin, or a subunit thereof, an antisense oligonucleotide, and an inducible promoter.

As used herein, the term "cytolethal distending toxin" (CDT) refers to a family of multisubunit toxins produced by a variety of bacteria. Each CDT is capable of inducing cell cycle arrest at G2/M in a variety of cell types, including Chinese Hamster Ovary (CHO), Hela, Hep-2, Vero, CaCo-2, human keratinocyte cell line (HaCat), hamster lung (Don) fibroblast and human T lymphocyte cells. (Johnson, W. and Lior, H., 1988, Micorbial Pathogenesis, "A new heat labile cytolethal distending toxin (CLDT) produced by *Campylobacter* spp.," Vol 4: pp. 115-126; Pickett, C. and Whitehouse, C., 1999, Trends Microbiol, "The cytolethal distending toxin family," Vol. 7(7): pp. 292-7). The cell cycle arrest results in a cessation of cell division. The CDTs are also capable of producing other effects, such as progressive cellular distention, in some of these cell types. Further, at least two cell types, Y-1 adrenal and NIH 3T3 fibroblast cells, are not killed in response to CDTs (Elwell, C. and Dreyfus, L., 2000, Molecular Microbiology, "DNase I homologous residues in CdtB are critical for cytolethal distending toxin-mediated cell cycle arrest," Vol 37(4): pp. 952-963).

A complete CDT represents a multiunit assembly of gene products from at least three genes: cdtA, cdtB, and cdtC. The genes for the CDTs have been cloned and characterized from a variety of bacterial species, including *Haemophilus ducreyi; Cimpylobacter jejuni*, and *Escherichia coli*, (see below).

As used herein, the term "B subunit", as it relates to a specific subunit of the multiunit CDT, refers to the product of the cdtB gene.

As used herein, the term "antisense oligonucleotide" refers to an oligonucleotide that has at least a partially complementary sequence to another oligonucleotide (the "sense oligonucleotide") such that the antisense is able to hybridize to the sense oligonucleotide.

As used herein, the term "inducible promoter" refers to a transcriptional promoter that promotes transcription of appropriate genes when certain environmental conditions are present.

As used herein, the term "heat shock promoter" refers to an inducible promoter that promotes transcription of appropriate genes when one ore more of a variety of stressful environmental conditions are present, including elevated temperatures (i.e., heat shock) and oxidative stress.

As used herein, the term "segment of a heat shock promoter" refers to a portion of a whole heat shock promoter.

As used herein, the term "strictly inducible by heat shock" refers to an ability of a heat shock promoter or segment thereof to promote transcription of appropriate genes at high level under heat shock conditions, while substantially not promoting higher transcription levels under other stressful, non-temperature related conditions, such as oxidative stress.

As used herein, the term "non-homologous end-joining DNA repair mechanism" refers to the DNA repair mechanism that operates to repair double-strand breaks in DNA in eukaryotic cells by blunt end ligation. The enzyme complex that accomplishes this repair mechanism includes the proteins ku70 and ku80, the DNA-dependent protein kinase (DNA-Pkes), and the DNA ligase IV, which functions in conjunction with the protein XRCC4. The ku70 and ku80 proteins form a dimer that binds the DNA double-strand end, and the repair mechanism operates by ligating the blunt ends created by the double strand break.

As used herein, the term "hybridization" refers to cumulative hydrogen bonding between complimentary nucleoside or nucleotide bases in a pair of oligonucleotides. The cumulative bonding, when sufficient, bonds the oligonucleotides to each other.

As used herein, the term "complimentary" refers to the ability of a pair of nucleoside or nucleotide bases to specifically bond with each other through hydrogen bonding. For example, in DNA, Adenine (A) and Thymidine (T) are complementary bases, and Cytosine (C) and Guanine (G) are complementary bases. The same is true in RNA, except that Uracil (U) is complimentary to Adenine (A).

As used herein, the term "oligonucleotide" refers to an oligomer or polymer of ribonucleic acid (RNA) or deoxyribonucleic acid (DNA), or mimetics thereof. The term encompasses oligers and polymers that include naturally occurring bases, non-naturally occurring bases that function similar to natural bases, and combinations thereof.

As used herein, the term "polynucleotide" refers to an oligomer or polymer of RNA or DNA in the same manner as an "oligonucleotide". The difference between the two terms is merely one of relative size: a polynucleotide refers to a larger entity, which may contain one or more oligonucleotides.

2. Description of Preferred Embodiments and Methods

In one aspect, the invention provides a construct for use in cytolethal gene therapy procedures. The construct is preferably contained within a vector, and preferably includes a first polynucleotide having a nucleotide sequence that encodes a gene for a B subunit of a CDT, a second polynucleotide having a nucleotide sequence that encodes an antisense oligonucleotide that inhibits expression of a nucleic acid encoding a DNA repair protein, and an inducible promoter operably linked to the first and second polynucleotides.

Essentially any agent that can contain the constructs according to the present invention can be used as the vector. Indeed, a wide variety of agents are recognized as being suitable for use in gene therapy procedures, and any of these suitable vectors can be utilized in the present invention. U.S. Pat. No. 6,093,567 to Gregory, et al., for GENE THERAPY FOR CYSTIC FIBROSIS provides a detailed discussion of some suitable vectors. Examples of known vectors that are suitable for use in the present invention include polymeric molecules, genetic cassettes, plasmids, phages, viruses, and pseudoviruses. Viruses are currently the most frequently used vectors in gene therapy, and several types of virus vectors can be used in the present invention. Examples of suitable virus vectors include papoviruses, lentiviruses, adenoviruses, adeno-associated viruses, vaccina viruses, herpes viruses, and retroviruses.

The following United States Patents provide descriptions of several types of viral vectors: U.S. Pat. No. 6,140,111 to Riviere, et al. for RETROVIRAL GENE THERAPY VECTORS AND THERAPEUTIC METHODS BASED THEREON; U.S. Pat. No. 6,106,826 to Brandt, et al. for REPLICATION COMPETENT, AVIRULENT HERPES SIMPLEX VIRUS AS A VECTOR FOR NEURAL OCCULAR GENE THERAPY; and U.S. Pat. No. 6,140,087 to Graham, et al. for ADENOVIRUS VECTORS FOR GENE THERAPY.

Preferably, the vector comprises a viral vector. Particularly preferably, the vector comprises an adenovirus vector.

It should be noted that the construct of the present invention itself can be considered a vector in accordance with the present invention. That is, the construct comprising the gene encoding the CDT B subunit gene, the antisense oligonucleotide, and the inducible promoter operably linked to these elements can, by itself, comprise the vector of the present invention. Naked DNA can be used in gene therapy procedures to deliver the gene of interest to a particular cell. This approach may be desired if the advantages of using other vector types, such as viral vectors, are not desired. For example, the inventor has discovered that the B subunit produces toxicity not only in the original cell, but also in some of the immediately surrounding cells. As a result, the need for a viral vector and its ability to replicate, repackage daughter vectors, and deliver the construct to the surrounding cells may be eliminated. In this case, use of the construct itself, i.e., naked DNA, as the vector may be suitable.

The first polynucleotide has a nucleotide sequence that encodes a gene for a B subunit of a CDT. The B subunit of CDTs displays enzymatic activity similar to that of DNAse I. (Lara-Tejero M. and Galan, J.; 2000, Science, "A Bacterial Toxin That Controls Cell Cycle Progression as a Deoxyribonuclease I-Like Protein", Vol 290: pp. 354-357; Elwell, C. and Dreyfus, L., 2000, Molecular Microbiology, "DNase I homologous residues in CdtB are critical for cytolethal distending toxin-mediated cell cycle arrest," Vol 37(4): pp. 952-963). That is, the β subunit has endonuclease activity, and can cause disruption of chromatin structures (Lara-Tejero M. and Galan, J.; 2000, Science, "A Bacterial Toxin That Controls Cell Cycle Progression as a Deoxyribonuclease I-Like Protein", Vol 290: pp. 354-357). This DNAse I activity may be responsible for the ability of the CDT to arrest the cell cycle (Elwell, C. and Dreyfus, L., 2000, Molecular Microbiology, "DNase I homologous residues in CdtB are critical for cytolethal distending toxin-mediated cell cycle arrest," Vol 37(4): pp. 952-963).

The B subunit of a CDT is encoded by the cdtB gene. The cdtB gene has been cloned and characterized from a variety of organisms, including *Haemophilus ducreyi* (Cope, L., Lumbley, S., Latimer, J., Klesney-Tait, J., Stevens, M., Johnson, L., Purven, M., Munson, R., Lagergard, T., Radolf, J. and Hansen, E., 1997, Proc. Natl. Acad. Sci. USA, "A diffusible cytotoxin of *Haemophilus ducreyi*," Vol 94: pp. 4056-4061) (SEQ ID 1 which encodes SEQ ID NOS 10-12), *Campylobacter jejuni* (Pickett, C., Pesci, E., Cottle, D., Russell, G., Erdem, A. and Zeytin, H., 1996, Infection and Immunity, "Prevalence of Cytolethal Distending Toxin Production in *Campylobacter jejuni* and Relatedness of *Campylobacter* sp. cdtB Genes," pp. 2070-2078) (SEQ ID 2 which encodes SEQ ID NOS 13-16), and *Escherichia coli* (Scott, D., and Kaper, J., 1994, Infection and Immunity, "Cloning and Sequencing of the Genes Encoding *Escherichia coli* Cytolethal Distending Toxin," pp. 244-251; (SEQ ID 3 which encodes SEQ ID NOS 17-19) Pickett, C., Cottle, D., Pesci, E., and Bikah, G., 1994, Infection and Immunity, Cloning, Sequencing, and Expression of the *Escherichia coli* Cytolethal Distending Toxin Genes," pp. 1046-1051) (SEQ ID 4 which encodes SEQ ID NOS 20-22). The sequencing information for these various cdtB genes reveal that considerable heterogeneity among cdtB (and cdtA and cdtC, see below) genes may exist (Pickett, C., Pesci, E., Cottle, D., Russell, G., Erdem, A. and Zeytin, H., 1996, Infection and Immunity, "Prevalence of Cytolethal Distending Toxin Production in *Campylobacter jejuni* and Relatedness of *Campylobacter* sp. cdtB Genes," pp. 2070-2078). Indeed, the predicted amino acid sequences for the proteins encoded by the cdtB genes listed as SEQ ID 3 and SEQ ID 4 share only 55-56% identity, despite being from different strains of the same bacteria (Pickett, C., Pesci, E., Cottle, D., Russell, G., Erdem, A. and Zeytin, H., 1996, Infection and Immunity, "Prevalence of Cytolethal Distending Toxin Production in *Campylobacter jejuni* and Relatedness of *Campylobacter* sp. cdtB Genes," pp. 2070-2078, analyzing sequences presented in Scott, D., and Kaper, J., 1994, Infection and Immunity, "Cloning and Sequencing of the Genes Encoding *Escherichia coli* Cytolethal Distending Toxin," pp. 244-251 and Pickett, C., Cottle, D., Pesci, E., and Bikah, G., 1994, Infection and Immunity, Cloning, Sequencing, and Expression of the *Escherichia coli* Cytolethal Distending Toxin Genes," pp. 1046-1051).

Any cdtB gene can be used in the first polynucleotide of the construct of the present invention, so long as the gene product possesses the desired toxicity. The B subunit represents the product of the suicide gene of the construct. Accordingly, any cdtB gene can be utilized so long as is encodes a gene product that possesses the toxicity associated with the B subunit protein, as discussed above. Preferably, the cdtB gene encodes a gene product that possesses the DNAse I-like activity associated with the B subunit. Also preferable, the cdtB gene encodes a gene product that is able to induce cell cycle arrest at G2/M in certain cells, such as CHO, HeLa, Hep-2, Vero, CaCo-2, HaCat, hamster lung fibroblast, and human T-lymphocyte cells (see, e.g., Johnson, W. and Lior, H., 1988, Micorbial Pathogenesis, "A new heat labile cytolethal distending toxin (CLDT) produced by *Campylobacter* spp.," Vol 4: pp. 115-126; and Pickett, C. and Whitehouse, C., 1999, Trends Microbiol, "The cytolethal distending toxin family," Vol. 7(7): pp. 292-7).

Preferably, the cdtB gene has the nucleotide sequence listed as SEQ ID 5 which encodes SEQ ID NO: 23). This sequence represents a cdtB gene cloned and characterized from *Escherichia coli* strain MBU. E 412 (Genbank accession number AF373206).

It should be noted that, while the CDTs are multiple subunit entities, the use of the other subunits, i.e., cdtA and cdtC, is not desirable in the present invention because these subunits appear to facilitate the entry of the B subunit into cells. If these subunits were included, widespread dispersion of the B subunit might be achieved, even though not intended. The distribution of the B subunit in the cells or tissue surrounding the cell in which the B subunit was originally introduced is, at this point, advantageously limited to those which the B subunit enters via the vector or on its own.

The second polynucleotide includes a nucleotide sequence that encodes an antisense oligonucleotide. Antisense oligonucleotides specifically hybridize with another oligonucleotide, the target or sense oligonucleotide, to interfere with the normal functioning of the target oligonucleotide. For example, if the target oligonucleotide is RNA, the functions to be interfered with include translocation of the RNA to the site of translation, translation of protein from the RNA, splicing of the RNA to yield one or more RNA species, and catalytic activity which may be engaged or facilitated by the RNA.

The use of antisense oligonucleotides is becoming more frequent and accepted in the areas of research and diagnostics. For example, antisense oligonucleotides that inhibit specific gene expression or protein translation are frequently used by those of ordinary skill in the art to elucidate the function of particular genes and/or protein. Further, antisense oligonucleotides are commonly used to distinguish between various functions of various members of a particular biological pathway. Also, antisense oligonucleotides are used to study the relationship between seemingly unrelated biological entities.

Those of ordinary skill in the art have also harnessed the use of antisense oligonucleotides as therapeutic agents. Antisense oligonucleotides have been proposed and used as therapeutics in a variety of disease conditions in animal and man. Indeed, antisense oligonucleotides have been administered to humans in a variety of clinical trials in a safe and effective manner.

U.S. Pat. No. 6,287,860 to Monia, et al. for ANTISENSE INHIBITION OF MEKK2 EXPRESSION and U.S. Pat. No. 6,251,873 to Furusako, et al. for ANTISENSE COMPOUNDS TO CD14 provide additional background information on antisense oligonucleotides and their use in research and medicine.

The second polynucleotide includes a nucleotide sequence that encodes an antisense oligonucleotide. The antisense oligonucleotide operates to inhibit the function of a target nucleic acid that is involved in a DNA repair mechanism. The CDT B subunit encoded by the first polynucleotide induces DNA damage in the host cell, and the antisense oligonucleotide operates to prevent the cell from utilizing its natural DNA repair mechanism(s) to repair the damage. This helps to ensure that the B subunit toxin will ultimately succeed in lysing the host cell.

Eukaryotic cells have a variety of DNA repair mechanisms that operate to repair damaged DNA.

As discussed above, the B subunit of CDTs possesses DNAse I-like activity, which presumably allows the toxin to arrest the cell cycle (see above; see also Lara-Tejero M. and Galan, J.; 2000, Science, "A Bacterial Toxin That Controls Cell Cycle Progression as a Deoxyribonuclease I-Like Protein", Vol 290: pp. 354-357; and Elwell, C. and Dreyfus, L., 2000, Molecular Microbiology, "DNase I homologous residues in CdtB are critical for cytolethal distending toxin-mediated cell cycle arrest," Vol 37(4): pp. 952-963). Thus, the B subunit has endonuclease activity that results in double strand breaks and blunt ends. Accordingly, the antisense oligonucleotide preferably interferes with the normal functioning of a sense oligonucleotide involved in a DNA repair mechanism that is able to repair these double-stranded breaks.

The non-homolgous end-joining mechanism is a DNA repair mechanism in eukaryotic cells that operates to repair double-strand breaks by blunt end ligation. The mechanism includes a series of proteins that accomplish the ligation. Specifically, the mechanism utilizes the ku70 and ku80 proteins, the DNA-dependent protein kinase (DNA-Pkes), and the DNA ligase IV, which functions in conjunction with the protein XRCC4. The antisense oligonucleotide can be any antisense that hybridizes to a target oligonucleotide in a manner that interferes with the functioning of the non-homolgous end-joining DNA repair mechanism. For example, the gene for the ku80 protein has been cloned.

Preferably, the antisense oligonucleotide interferes with the normal functioning of a target oligonucleotide that encodes a gene for the ku70 protein.

The cDNA encoding ku70 has been published.

The antisense oligonucleotide can be designed to interfere with the normal functioning of the appropriate gene (e.g., the gene encoding the ku70 protein) or an mRNA molecule transcribed from the gene. Because the ku70 participates in the activity of interest for the present invention (i.e., repair of DNA double-strand breaks) and it is not believed that the mRNA has any such participation, the antisense oligonucleotide preferably interferes with the normal functioning of the mRNA for the ku70 protein. This, it is preferred that the antisense oligonucleotide interferes with the translation of the ku70 protein from the mRNA.

It is known in the art that an antisense oligonucleotide need not hybridize to the entire length of the target nucleotide to achieve the desired interference with functionality. Indeed, it may be possible to determine a specific site or sites within the target oligonucleotide that can be targeted such that the desired interference occurs. Such sites can be determined by gene walk experiments known to those skilled in the art. In these experiments, a series of overlapping antisense oligonucleotides are evaluated for their ability to achieve the desired interference.

However, interference can be assured by the use of an antisense oligonucleotide that is a "full length" antisense. That is, the full length antisense is able to hybridize to the entire target oligonucleotide (e.g., the gene or mRNA). Because of this full length hybridization, the desired interference is assured to occur. Thus, in the present invention, the antisense oligonucleotide preferably is a full length antisense for the ku70 mRNA. The full length antisense, therefore, preferably is able to hybridize to the mRNA from at least the translation initiation codon (5'-AUG) (also referred to as the "start codon") to the translation termination codon (also referred to as the stop codon). The step codon in mRNA can be one of three sequences: 5'-UAA, 5'-UAG, and 5'UGA. It should be noted that some genes have alternative translation initiation codons having the following sequences: 5'GUG, 5'UUG, or 5'CUG. Further, the following sequences have been shown to function as start codons in vivo: 5' AUA, 5' ACG and 5'-CUG.

It is also known in the art that an mRNA may have several alternative translation initiation codons, any one of which may be preferentially used in a particular cell or tissue, or under a particular set of conditions. To the extent such multiple start codons are present in the target oligonucleotide, it is preferred that the antisense oligonucleotide be able to hybridize to all start codons present. This ensures the desired interference with the mRNA function.

It will be appreciated by those of skill in the art that an antisense oligonucleotide need not be 100% complimentary to its target oligonucleotide to achieve hybridization that accomplishes the desired interference. Indeed, only a sufficient degree of complimentarity is required. The sufficient degree of complimentarity required is that degree which avoids non-specific binding to non-target oligonucleotides while allowing enough hybridization to the target oligonucleotide to achieve the desired interference with the function of the target oligonucleotide.

Considering the above, a particularly preferred antisense oligonucleotide has a sequence complimentary to the sequence listed as SEQ ID 6 which encodes SEQ ID NO: 24).

The construct of the present invention includes an inducible promoter operably linked to the first and second polynucleotides. That is, the construct includes an inducible promoter that is able to initiate the transcription of the B subunit gene and the antisense oligonucleotide.

Inducible promoters are those promoters able to induce transcription of appropriate genes when certain environmental conditions are met. A variety of inducible promoters, which correspond to a variety of environmental conditions that induce the promoters, are known to those skilled in the art. Examples include the arabinose promoter, the metallothioneine promoter, and the heat shock promoters. The use of an inducible promoter is desired because it is desirable to regulate the expression of the B subunit and antisense by environmental conditions, such as temperature (see below). Accordingly, any suitable inducible promoter can be utilized. The choice of inducible promoter should be made to ensure that the B subunit and the antisense oligonucleotide are not constitutively expressed. Also, the inducible promoter should promote the expression of these elements under only the environmental conditions that will be used to regulate the gene therapy procedure. The heat shock promoters provide suitable inducible promoters for use in the present invention. As indicated above, these promoters induce transcription when certain stressful environmental conditions are present, such as elevated temperatures and oxidative stress.

The human Hsp70B heat shock promoter is suitable for use in the present invention. The sequence for this promoter is listed in SEQ ID 7.

Preferably, the inducible promoter is strictly inducible by heat shock. This characteristic ensures that activation of transcription of the B subunit and antisense oligonucleotide will occur only in the presence of heat shock, which allows for tight regulation of the gene therapy procedure. This strict inducibility can be accomplished by using a segment of a heat shock promoter. Indeed, segments of the human Hsp70B heat shock promoter that are strictly inducible by heat shock have been determined (Schiller, P., Amin, J., Ananthan, J, Brown, M., Scott, W., and Voellmy, R., 1988, J. Mol. Biol., "Cis-acting Elements Involved in the Regulated Expression of a Human HSP70 Gene, Vol. 203: pp. 97-105 (SEQ ID NO: 8); Voellmy, R., Ahmed, A., Schiller, P., Bromley, P., and Rungger, D., 1985, Proc. Natl. Acad. Sci. USA, "Isolation and functional analysis of a human 70,000-dalton heat shock protein gene segment," Vol. 82: pp. 4949-4953). A sequence of a preferred such segment appears as SEQ ID 9 (which encodes SEQ ID NO: 25). Molecular vectors utilizing such a segment are readily available from commercial sources, and include the p2500-CAT and pD35X vectors available from Stressgen Biotechnologies Corporation of Victoria, British Columbia, Canada.

It will be appreciated by those skilled in the art that the construct of the present invention can be made according to standard molecular biology and genetic engineering techniques. Such techniques include using expression vectors, digesting an expression vector with a restriction endonuclease enzyme, and isolating a desired vector product. Also, packaging a construct of the present invention into a vector such as a viral vector, if desired, can be accomplished according to techniques known to those skilled in the art.

The present invention also provides methods of conducting cytolethal gene therapy. The methods according to this invention utilize vectors according to the invention, and comprise delivering the vector to a desired cell and placing the cell under environmental conditions appropriate to induce the promoter. As a result, the B subunit and antisense oligonucleotide are expressed. The B subunit causes DNA damage in the cell, and the natural DNA repair mechanism of the cell is hindered by the antisense oligonucleotide. Ultimately, this results in the death of the cell.

The vector used in the methods of the invention can be any vector in accordance with the invention, as described above. Thus, viral vectors as well as plasmids and naked DNA vectors, in addition to other suitable vectors, can be utilized. Preferably, a vector according to the preferred embodiment of the invention is used. That is, it is preferred to utilize an adenoviral vector containing a polynucleotide encoding a cdtB gene, an antisense oligonucleotide that inhibits the expression of ku70, and a segment of a heat shock promoter that is strictly inducible by heat shock and that is positioned to promote expression of the cdtB gene and the antisense oligonucleotide.

The cell can comprise any eukaryotic cell in which the vector can achieve its function. Thus, the cell should contain DNA and should have a natural DNA repair mechanism. Essentially any eukaryotic cell, therefore, can be used in the procedure.

As a controllable cytolethal procedure, the methods of the present invention provide techniques suitable for killing one or more cells of interest. As such, the methods are well-suited for eliminating undesired cells from a tissue or host. An example of such a type of cell is a cancerous cell, which may be contained in a solid tumor. The methods can be used on a variety of solid tumors, including colon, prostate, breast, lung, skin, liver, bone, pancreas, ovary, testes, bladder, kidney, brain, nerve, and head and neck tumors.

Accordingly, the cell is preferably a cancerous cell contained within a solid tumor.

Delivering the vector to the desired cell or cells can be accomplished by any suitable technique. For example, systemic delivery routes such as intravenous injection can be utilized if the vector is able to specifically enter the desired cell. Preferably, however, the vector is directly delivered to the cell or tissue of interest. This direct delivery is preferably accomplished by a direct injection technique. Direct injection can be accomplished using a syringe, needle, or other delivery device suitable for delivering other therapeutic agents to tissue. When the cell of interest is in a solid tumor, the vector can be injected with a standard syringe into the tissue mass. Preferably, using this technique, the syringe is inserted into the tissue at a depth and position that ensures delivery of the vector to the approximate geometric center of the tissue mass. Alternatively, the position at which the vector is delivered can be varied according to the needs of the procedure being conducted. Also, microinjection techniques can be utilized to directly place the vector inside of the cell of interest.

The quantity and concentration of vectors delivered to a cell and/or tissue of interest can be optimized based on a number of parameters, including the ability of the vector to replicate and the number of cells in which treatment is desired. Preferably, when an adenoviral vector is used with a solid tumor, a multiplicity of infection of between approximately 1 and 100 is used.

As indicated above, the methods of the present invention also include placing the desired cell under environmental conditions appropriate to induce the inducible promoter. Thus, the details of this step will depend on the nature of the inducible promoter, and may include adding a particular compound to the cellular environment or inducing a particular type of environmental stress.

When a vector according to the preferred embodiment is utilized, i.e., the inducible promoter is a heat shock promoter, this step involves elevating the temperature of the cell (or the tissue or tumor it is contained in) to a temperature suitable for inducing the promoter. This requires elevating the temperature to above normal body temperature.

For example, in procedures involving human cells, the temperature of the cell and/or tissue is elevated to a temperature above normal human body temperature, 37° C. The temperatures and ranges discussed above are for human hosts, but it will be readily recognized that appropriate temperatures can be induced in other animals by determining the normal body temperature of the animal and elevating the temperature of the tissue to a temperature above the normal body temperature. The elevated temperature need only be suitable for the heat shock promoter utilized in the vector.

The elevating of the temperature of the cell can be referred to as inducing hyperthermia. The use of hyperthermia with tumors has some beneficial affects (see, Dewey, W. and Freeman, M., "Rationale for Use of Hyperthermia in Cancer Therapy," pp. 372-378) and thus, the use of heat shock promoters has benefits that may be two-fold: regulation of expression of vector components, and hyperthermic benefits to tumor therapy.

While hyperthermia induces the heat shock promoters, it may not be desirable to increase the temperature of other tissues of the animal undergoing treatment. Therefore, the hyperthermia is preferably localized to the cell and/or tissue of interest. Devices and methods of accomplishing localized hyperthermia are known (see, for example, U.S. Pat. No. 6,176,857 to Ashley for a METHOD AND APPARATUS FOR APPLYING THERMAL ENERGY TO TISSUE ASYMMETRICALLY) and can be used to accomplish the desired effect. Alternatively, hyperthermia can be induced in the general anatomical area that contains the tissue of interest.

The effect of the hyperthermia is likely to be greatest when the elevated temperature is maintained in the tissue for a duration of time. Therefore, it is preferred that the elevated temperature be maintained in the tissue of interest for a set period of time.

The increase in the temperature of the cell and/or tissue of interest will depend upon several factors, including the type of procedure being conducted. Preferably, the temperature of the tissue of interest is elevated to between approximately 38° and 45° C. For procedures involving a vector utilizing the human hsp70B promoter, it is preferred that the temperature of the tissue is elevated to approximately 41° C.

The length of time during which the temperature of the cell and/or tissue of interest remains elevated will also depend upon several factors. Preferably, for procedures in which is desirable to enhance the diffusion of the vector through the tissue of interest, such as a solid tumor, the elevated temperature is maintained until the vector diffuses through the tissue. That is, it is preferable that the elevated temperature be maintained in the tissue of interest until the vector diffuses throughout the tissue of interest. Appropriate times can be determined for specific vector and tissue combinations. The time can be determined for the vector being utilized as appropriate by standard methods. Preferably, the elevated temperature is maintained in the tissue of interest for between approximately one and 72 hours. The duration of maintaining the elevated temperature may be brief, extended, or even intermittent in nature. The preferred duration of hyperthermia will depend on several factors, and should be optimized accordingly. Appropriate end points for hyperthermia include completion of diffusion of the vector through the tissue of interest.

Inducing hyperthermia in accordance with the methods of the present invention can be accomplished in a variety of manners. Essentially any technique that produces an appropriate increase in temperature in the cell and/or tissue of interest can be used. Preferably, techniques of raising temperature in tissue that allow for maintaining the elevated temperature over a period of time are used.

Several methods of inducing hyperthermia in tissue have been described. U.S. Pat. No. 6,167,313 to Gray, et al. provides an overview of several techniques and methods. Any standard technique can be used to accomplish the desired hyperthermia. For example, an ultrasonic transducer can be employed to deliver a localized increase in tissue temperature. For an example of methods and apparatuses in accordance with this category, see U.S. Pat. No. 5,620,479 to Diedrich. Alternatively, a technique commonly referred to as interstitial hyperthermia can be employed. Other alternative methods of inducing hyperthermia include exposing the tissue to microwave radiation (for example, see U.S. Pat. No. 5,861,021 to Thome et al. and U.S. Pat. No. 5,922,013 to Fallick) or magnetic induction (see the '313 patent).

The method employed to induce hyperthermia can be optimized based upon the nature of the tissue of interest. For example, for deep tissues, such as a tumor in prostate tissue, interstitial hyperthermia will likely offer a better ability to control the hyperthermia. For surface tissues, a simple device, such as an ultrasonic transducer, will be sufficient.

The references cited in this disclosure, except to the extent they may contradict any statements or definitions made herein, are each hereby incorporated by reference in their entirety.

The foregoing disclosure includes the best mode devised by the inventor for practicing the invention. It is apparent, however, that several variations in accordance with the present invention may be conceivable to one of ordinary skill in the relevant art. Inasmuch as the foregoing disclosure is intended to enable such person to practice the instant invention, it should not be construed to be limited thereby, but should be construed to include such aforementioned variations, and should be limited only by the spirit and scope of the following claims:

The invention claimed is:

1. A gene therapy vector, comprising:
   a first polynucleotide encoding a gene for B subunit of a cytolethal distending toxin; and
   a second polynucleotide encoding an antisense oligonucleotide that inhibits expression of a sense oligonucleotide encoding a DNA repair protein;
   wherein the first and second polynucleotides are operably linked to an inducible promoter;
   wherein the inducible promoter is a heat shock promoter;
   wherein the inducible promoter is a segment of a heat shock promoter that is strictly inducible by heat shock; and
   wherein the inducible promoter has a nucleotide sequence of SEQ ID 7.

2. The gene therapy vector of claim 1, wherein the gene is E. coli cdtB; and
   wherein the gene has a nucleotide sequence of SEQ ID 5.

3. The gene therapy vector of claim 1, wherein the second polynucleotide encodes an antisense oligonucleotide that inhibits expression of a sense oligonucleotide encoding a protein involved in the non-homologous end-joining DNA repair mechanism;
   wherein the protein is ku70; and
   wherein the second polynucleotide is complimentary to nucleotide sequence SEQ ID 6.

* * * * *

SEQUENCE LISTING

<160> NUMBER OF SEQ ID NOS: 25

<210> SEQ ID NO 1
<211> LENGTH: 2384
<212> TYPE: DNA
<213> ORGANISM: Haemophilus ducreyi

<400> SEQUENCE: 1

```
agaaaagata ttgaacaggt tctaacataa agtataataa aggttcatat gcttttttac      60
gatattatct ggtttggttt tatcaaaaaa aaggataaaa tgcgaagaac ttgtcctttt     120
aaatttaagg atggatctaa ggagagatat aatgaaaaag ttttaccta gtcttttatt     180
gatgggttca gtggcttgtt catcaaatca acgaatgaat gactattctc aacctgaatc     240
tcaatctgat ttagcaccta atcttcaac aatacaaccc caacctcaac ccctattatc     300
aaaaacacct tcaatgtcac tgaatttgct atcttcatcc ggaccgaata gacaggtatt     360
gccgtctgaa ccatcaaact ttatgacttt gatgggacaa aatggggcac tgttgactgt     420
ctgggcgcta gcaaaacgca attggttatg gcttatccc aatatatatt cgcaggactt     480
tggaaatatt cgtaattgga agatggaacc cggtaaacac cgtgaatatt ttcgttttgt     540
taatcaatct ttaggtacat gtgttgaagc ttacggtaat ggtttaattc atgatatttg     600
tagtctggac aaaattagcac aagagtttga gttattacct actgatagtg gtgcggttgt     660
cattaaaagt gtgtcacaag gcgttgtgt cacttataat cctgtaagta caacatttta     720
ttcaacagtt acattatcag tttgtgatgg cgcaacagaa ccatcacgtg atcaaacatg     780
gtatctcgct cccctgtat tagaagcaac agcggttaat taaactaagg agtttatatg     840
caatgggtaa agcagttaag tgtggttttc tgtgtgatgt tatttagctt ttcaagttat     900
gctaacttga gtgacttcaa agtagcaact tggaatctgc aaggttcttc agcagtaaat     960
gaaagtaaat ggaatattaa tgtgcgccaa ttattatcgg gagaacaagg tgcagatatt    1020
ttgatggtac aagaagcggg ttccttacca agttcggcag taagaacctc acgggtaatt    1080
caacatgggg gaacgccaat tgaggaatat acttggaatt taggtactcg ttcccgccca    1140
aatatggtct atatttatta ttctcgttta gatgttgggg caaaccgagt gaacttagct    1200
atcgtgtcac gccgtcaagc cgatgaagct tttatcgtac attctgattc ttctgtgctt    1260
caatctcgcc ctgcagtagg tatccgcatt ggtactgatg tattttttac agtgcatgct    1320
ttggccacag gcggttctga tgcggtaagt ctgattcgta atatcttcac tacttttaac    1380
tcatcatcat ccccaccgga aagacgagta tatagctgga tggttgttgg tgatttcaat    1440
cgtgcgccgg ctaatctgga agttgcatta agacaggagc ccgcagtgag tgaaaataca    1500
attattattg cgccaacaga accgactcat cgatctggta atattttaga ttatgcaatt    1560
ttacatgatg cacatttacc acgtagagaa caggcccgtg aacgtatcgg tgcaagttta    1620
atgttaaatc agttacgctc acaaattaca tccgatcatt ttcctgttag ttttgttcgt    1680
gatcgctaag gaggatatta tgaaaaaata tttattgagc ttcttattaa tcatgatatt    1740
ggctttggcg agtcatgcag aatcaaatcc tgatccgact acttatcctg atgtagagtt    1800
atcacctcct ccacgtatta gcttgcgtag tttgcttacg gctcaaccag ttaaaaatga    1860
tcattatgat tcacataatt acttgagtac acattgggaa ttaattgatt acaaaggaaa    1920
agaatatgaa aaattacgtg acggtggtac gttagttcaa tttaaagtgg ttggtgcagc    1980
aaaatgtttt gctttcctgg gcaaaggcac aactgattgt aaagatactg atcatactgt    2040
gtttaacctt attccaacta atacgggcgc gttttaatc aaagatgcac tattagggtt    2100
ttgtataaca agccatgact ttgatgattt gaagcttgaa ccttgtggag ttcagtgag    2160
tggtcgaacc ttttcgttgg cgtatcaatg ggggatatta cctccttttg gaccaagtaa    2220
aattttaata ccaccggtgc gaagaaatca gggtagctaa tgtttacat ataattgtat    2280
ttcttcaaat caagatcctt agtggggcga agaaatataa tgtcattatt gtgcttatgt    2340
```

```
taatgatcat gcaaaaatga gccaggcaga cgcagtaaga tcat              2384
```

<210> SEQ ID NO 2
<211> LENGTH: 2600
<212> TYPE: DNA
<213> ORGANISM: Campylobacter jejuni

<400> SEQUENCE: 2

```
tgctaaaata taagtgttta agatacatat aaattctacc tttaaaaaca acaaaataaa    60
acattttaa aaagcggaaa attataatga aattatgtt attattttct taaaaattta    120
aatacatatc aaggttttta atgcaaaaaa ttatagtttt tattttatgt tgttttatga   180
ctttttttct ttatgcatgt tcttctaaat ttgaaaatgt aaatcctttg gggcgttcat   240
ttggagaatt tgaagatact gatcctttaa aactaggact tgaacctact tttcctacca   300
atcaagaaat tccaagttta attagcggtg ctgatttagt acctattact cctattaccc   360
cacctttaac tagaacaagc aatagtgcca acaataatgc agcaaatggg atcaatcctc   420
gctttaaaga cgaagctttt aatgatgttt taattttga aaatcgccct gcggtttctg    480
attttttaac cattttaggc cctagcggag cagcttaac ggtttgggct ttagcacaag    540
gaaattggat ttggggctat actttaatcg atagcaaagg atttggcgat gctagagttt   600
ggcaactttt gctttatcct aatgattttg caatgattaa aaatgccaaa accaatactt   660
gtcttaatgc ttatggtaat ggaattgtcc attatccttg tgatgcaagc aatcacgcac   720
aaatgtggaa acttatccct atgagcaata cagcggttca aattaaaaat ttaggaaatg   780
gaaaatgcat acaagcacct attacaaatc tttatggtga ttttcacaag gttttaaaa    840
tttttaccgt agagtgtgca aaaaaagata attttgatca acaatggttt ttaactactc   900
cacctttttac cgcaaaaacct ttatatcgcc aaggagaggt acgatgaaaa aaattatatg   960
tttattttta tcttttaacc ttgcttttgc aaatttagaa aattttaatg ttggcacttg   1020
gaatttgcaa ggctcatccg cagccacaga aagcaaatgg agtgttagtg taagacaact   1080
tgtaagtgga gcaaacccct tagatatctt aatgatacaa gaagcaggaa ctttaccaag   1140
aacagccact ccaacaggac gccatgtgca acaaggtgga acaccattg atgaatatga   1200
gtggaattta ggaactcttt caaggcctga tagggttttt atttattatt ctcgcgttga   1260
tgtaggagct aatcgtgtaa atttagctat agtttcaaga atgcaagctg aagaagtgat   1320
tgttttacct ccacctacta cagtttcaag acccattata ggaattcgca atggaaatga   1380
tgctttttc aatatccatg ctttagctaa tggaggaaca gatgtaggag caattatcac   1440
agctgtagat gcacattttg caaatatgcc tcaagttaac tggatgatag cagggattt    1500
taaccgtgat ccttctacta taacaagtac agtggataga gaattagcaa atagaattag   1560
agtggttttt ccaactagcg caactcaagc aagcggaggg actcttgatt atgcaattac   1620
aggaaattca aatagacaac aaacctatac tccaccgctt ttagctgcga ttttaatgct   1680
tgcaagttta agatctcata tagtttcaga tcattttcca gtaaattta gaaaatttta   1740
ggacatttaa tatgaaaaaa attattactt tgttttttat gtttataact ttagcctttg   1800
caactcctac tggagatttg aaagatttta ccgaaatggt ttctataaga agcttagaaa   1860
cgggaatttt tttaagcgcc tttagggata cctcaaaaga tcctattgat caaaattgga   1920
atattaaaga aattgtttta agcgatgagt taaaacaaaa agataaatta gctgatgaac   1980
ttccttttgg ttatgtgcaa tttacaaatc caaaagaaag cgatctttgt ttagccatct   2040
```

```
tagaagatgg aacctttgga gcaaaatctt gtcaagatga tctaaaagat ggtaaattag    2100
aaactgtatt ttctataatg ccaacaacaa cttcagctgt gcaaattcgt tctttagttt    2160
tggaatctga tgaatgtata gtaactttt  ttaatccaaa tattcctata caaaaacgct    2220
ttggaatagc cccttgcacc ctagatccta ttttttttgc tgaagtaaat gaactaatga    2280
ttataacccc accttaaca  gctgctaccc ctttagaata agattttat  cttgttctat    2340 ttttatattt atttaatatt tatgatatta ctaaaataca caaataatt  aataataata    2400 caatgtaatt taccttgctc tataattttt ttattttaat gtaattttt  gttacaataa    2460 atttatacat aataattatc ttggaggaaa aattggaaca aattttaaca tggcaacaaa    2520
tttatgaccc ttttcaaat  atttggctaa gtgctttagt ggcattttta cctatactat    2580
gttttttagt ttgtttggtt                                                 2600

<210> SEQ ID NO 3
<211> LENGTH: 2305
<212> TYPE: DNA
<213> ORGANISM: Escherichia coli

<400> SEQUENCE: 3
tattgaatag ttttgggggg aatataaaga attatatttg agtatgctgt tgtgactct      60 gggaataata acgagcatta taataaactt gtttgttttt ctggtttcgc atttcctcat    120
taatcttgtt ggtaatattt tcgttgcttt gttgtttcta ttttttttata aagaagaggt    180 ggtgcagagg aggaaataca gtggataaaa aactaattgc atttttgtgc acacttataa    240
ttactggttg ctcgaatggg atcggtgatt caccttcacc tccgggaaaa aatgtagaat    300
tggttggaat ccctggacaa ggtattgcag tgacttcaaa cggtgcaact ccaacacttg    360
gagccaacaa cactgagttt cctgaagttt caataatgag cactggtggg gcgctgctta    420
ctatttgggc cagacctgtt cgtaactggc tttgggggta tactcctttt gattcagtaa    480
attttggtga gaatcggaac tggaaggttg tggatgggaa agatgccggc acagtgaaat    540 tgttaatgt  tgcccagggg acttgcatgg aggcctttaa aaacggggtg atacataata    600
cctgtgatga taactcgtta tctcaggagt ttcagttact gccttctact aatggtaatg    660
tgcttataag aagtagtgcc ttgcagacgt gtataagagc agactattta agcagaacta    720
tattgtcacc gtttgctttt acaatcaccc ttgagaaatg ccctggtgca aaagaagaaa    780
cgcaagaaat gctatgggca ataagtccac ctgtcagagc ggcaaaacca aatctgatta    840
agccagagtt aagaccattc agaccattgc caattccacc tcatgacaaa cctgatggaa    900
tggagggagt atgaaaaaat tattattcct gttaatgatt tgccgggta  ttctcttttgc   960 agatttaagc gattttaaag ttgcaacctg gaatttgcag ggttcaaatg caccgacaga   1020
aaataaatgg aacacacatg tccgacaact tgttacggga agtggtgctg ttgatatcct   1080
gatggttcag gaggcagggg cagtaccagc ttctgcaacg ttgactgagc gagaatttag   1140
cactcctggt attccgatga atgagtatat ctggaatacc ggaaccaata gtcgcccaca   1200
ggagttgttt atatatttct cacgtgttga tgcattcgct aacagagtaa atcttgcgat   1260
tgtttcaaac agaagagctg atgaggtgat tgtattacct cctccaactg ttgtatcacg   1320
accgatcatc ggcattagaa ttggtaatga tgttttcttc tcaacccatg cattggcgaa   1380
tcggggcgtg gattcaggag caattgtaaa tagtgttttt gagttcttca acagacaaac   1440
ggatcctata agacaggccg ctaactggat gattgcagga gattttaacc gttcaccggc   1500
tacactattt tcaactcttg aaccagggat tcgcaatcat gtaaatatta ttgctccacc   1560
```

```
agatccaacg caagccagtg gtggtgttct tgattatgca gtagttggaa attcagtgag    1620 cttttgttctt cctctgttga gggcctcgtt gttattcgga ttattaagag ggcaaattgc    1680
ctctgatcat tttccggttg gctttattcc tggaagagga gcaagaagat gaaaacagtt    1740
attgtgtttt ttgttttact gctgacaggt tgtgcttctg aacctgcaaa tcagcgtaat    1800
cttcttactc agtttgtcgg caacaatgcc cctgtagacc ctgaacccag tccagtattg    1860
gttaatatca gaaacgttct tacaggggggg ataatccgaa atcctgttgg cagtgacttt    1920
aatgtaaata attgggttat atctgaagta aagactaatg attttggattt gatatcggca    1980 ccgggagggc atgttcagat taaaaatcct gatggcaatg aatgctttgc tattctaaac    2040
gggcaattgg cagtggctaa gcagtgctct gaaagtgacc gtaacgcatt gtttacattt    2100
ataaccagtg atactggggc tgtgcaaatc aagtcaatag gaagcggtca atgcctaggg    2160
aatggagaga gcattacaga tttcaggtta aaaaaatgtg ttgatgatct tgggcgtcct    2220
tttgatacgg tgccgccggg gttactctgg atgctgaatc caccattatc tccggcaata    2280
atgtctccat taacgagctg atctg                                           2305

<210> SEQ ID NO 4
<211> LENGTH: 2600
<212> TYPE: DNA
<213> ORGANISM: Escherichia coli

<400> SEQUENCE: 4
attaacaaat tacaacaaag atcacattaa ataaaaattg acaattgacc tgtagttcat      60
catttgtaaa ttcatgattt atatcaatca cgctttgtgt tcggagtaag cttataaatt     120
acaaaaacga ttaataaaaa aaccacacaa taatattaaa taaaaatacg gtatcgactg     180
cttttgtttc aaaaggaatt gctattaaaa ctatatactt tcatttagtt ttatcaatta     240
atgcataact tcaaatgtaa catcaaaaac aatacacctc aaaacaatca cacaaagcaa     300
caaggacacc caaacaacta aggcactaat aaaaaggaga gtcccaatgt aattcttta     360 ttcttccatt aatttctact atctttatca taataaggac cataataatg gctaacaaac     420
gtacacctat ttttatagct ggaatcttga tccccatttt attaaatggt tgctcatcag     480
gaaaaaataa agcttatctt gaccccaaag ttttccctcc tcaagtggaa ggaggaccaa     540
ccgttccttc ccccgatgag cccggacttc cattgcccgg gccaggaccg gcgctgccca     600
caaatggcgc aatccctatc cctgaaccag gtaccgcacc cgcagtatct ttaatgaata     660
tggatggctc agttctaaca atgtggagcc gcggagctgg ttcatcgtta tgggcgtatt     720
atatcggcga ctccaattca tttggggaac tacgtaattg gcagattatg cccggaacca     780
ggccaaatac gatacagttt cgcaatgtag acgttggtac ctgtatgaca gtttcccag     840 gatttaaagg gggagtacaa cttttctacag caccttgcaa gtttggaccg gaacgtttcg     900
atttccagcc aatggcaaca cgcaatggta attaccagtt aaaatcttta tctacaggtt     960
tatgcatcag agcgaatttt ttaggaagaa caccatcatc tccgtacgca acgacattaa    1020
caatggagcg ttgcccatca agtggagaga aaaactttga attcatgtgg tccataagcg    1080
aaccattaag gcctgctctg ccactattg ccaagccaga aatacgccca tttccaccac    1140
agccaataga accagatgag cattcaactg gaggagaaca atgaaaaaat atattatatc    1200
tctgatagtt tttttatcat tttacgctca agcagattta actgattttc gcgttgcgac    1260
ctggaatctt caaggtgcat ccgctacgac tgaaagtaaa tggaatataa atgtccggca    1320
```

-continued

```
attaatttct ggtgaaaatg ctgtagacat tttagctgta caagaggcag gctctccgcc    1380
gtcaacggct gtagatacag gtacacttat tccttcccca ggaattcccg tccgagagct    1440
tatctggaac ttgtcgacaa atagcaggcc acagcaagta tatatatatt tttccgctgt    1500
tgatgccctc ggtggaagag tcaatcttgc tctggttagc aatcggcggg ccgatgaagt    1560
gtttgttctt agtcctgtaa gacaaggtgg acgaccattg cttggcatac gaattggtaa    1620
tgatgcattt ttcactgcac acgccatagc tatgcgaaac aatgatgccc cggctcttgt    1680
tgaggaagtg tataacttct tccgcgacag cagagaccca gtacaccagg cgcttaactg    1740
gatgattctt ggtgatttca accgtgaacc tgcggattta gagatgaacc ttactgttcc    1800
cgtaagaagg gcatcagaaa ttatttcacc agcggcggca acacaaacca gccagcgaac    1860
attagattat gcagtagcag gaaactctgt ggcatttaga ccatctccgc tacaagcggg    1920
aattgtatat ggagccagga gaactcaaat atcttcagat catttccctg ttggcgtatc    1980
cagacgataa aagaggctat cataatgaaa aaattagcaa ttgttttttac tatgctgcta    2040 atagctggat gctcttcatc acaggattca gctaacaatc agatagatga attaggaaaa    2100
gaaaacaatt ctctattcac attccgcaat atccaaagtg gcttaatgat ccataatgga    2160
ttacatcagc atggccgaga gactattgga tgggaaatag tccctgtgaa acacctgaa     2220 gaagcacttg ttaccgatca aagcgggtgg ataatgattc gaacgccaaa cacagaccaa    2280
tgtttaggga cgcctgatgg aaggaacctg ctaaaaatga cgtgtaattc aacagctaag    2340
aaaactttgt tttctctcat accgtcaaca acaggggcag tacaaatcaa aagcgttctg    2400
tctgggcttt gtttcttaga tagtaaaaat agcggattaa gttttgaaac ggggaaatgc    2460
attgctgact tcaaaaaacc atttgaagtt gtaccacaga gccatttgtg gatgttgaac    2520
ccattaaata ctgaatcgcc tattatttaa tcccatcatc gcattttgcc gggcacataa    2580
aaagcattat cataataagt                                                2600
```

<210> SEQ ID NO 5
<211> LENGTH: 468
<212> TYPE: DNA
<213> ORGANISM: Escherichia coli

<400> SEQUENCE: 5

```
tgaaaataaa tggaacacac atgtccgaca acttgttacg ggaagtggtg ctgttgatat      60
cctgatggtt caggaggcag gggcagtacc agcttctgca acgttgactg agcgagaatt     120
tagcactcct ggtattccga tgaatgagta tatctggaat accggaacca atagtcgccc     180
acaggagttg tttatatatt tctcacgtgt tgatgcattc gctaacgag taaatcttgc      240 gattgtttca aacagaagag ctgatgaggt gattgtatta cctcctccaa ctgttgtatc     300
acgaccgatc atcggcatta gaattggtaa tgatgttttc ttctcaaccc atgcattggc     360
gaatcggggc gtggattcag gagcaattgt aaatagtgtt tttgagttct tcaacagaca     420
aacggatcct ataagacagg ccgctaactg gatgattgca ggagattt                  468
```

<210> SEQ ID NO 6
<211> LENGTH: 2743
<212> TYPE: DNA
<213> ORGANISM: Homo sapiens

<400> SEQUENCE: 6

```
gcgggccgtt atccatttgt gttgttcgcc agctaggcct ggcctcgtcc cgcttcgctc      60
ggtcggtctc gcgcgccccc atagccttgc tagagggtta gcgttagcct taagtgtgcg    120
```

```
aatccgagga gcagcgacag actcgagacc acgctccttc ctcgggaagg aggcggcacc    180
tcgcgtttga ggcccgcctg cgtttgaggc ccgcctgcgc ttgcggcccg cctgcgcttg    240
aggcctgtct gcgtttgaga tctcattggg cgtgattgag gaatttgggg aggttttgg     300 gcggtattga ggacgagggg gtccgttagt cagcatagaa tcctggagcg ggaatccctc    360
accgtctaaa tggcgtcggg ggcgggacct ccgggatctg gcttccgcgg gccgccgccg    420
gccctgaaac gtgagggata gctgagatga ggcagctact gggatggccc ccatgcgcat    480
ttacatgcag tccgactgcc gagctttcga ggcagcagga tttaccgtcc acattcctca    540
ctactaacca agcttttaga acagatctca caagaaccta gaggtcggta ttttttcgat    600
ttaaatttgc ctgttactga cgttaacgtc tttcgcctag tgagcagtag ccaacatgtc    660
agggtgggag tcatattaca aaaccgaggg cgatgaagaa gcagaggaag aacaagaaga    720
gaaccttgaa gcaagtggag actataaata ttcaggaaga gatagtttga ttttttggt     780 tgatgcctcc aaggctatgt tgaatctca gagtgaagat gagttgacac cttttgacat      840
gagcatccag tgtatccaaa gtgtgtacat cagtaagatc ataagcagtg atcgagatct    900
cttggctgtg gtgttctatg gtaccgagaa agacaaaaat tcagtgaatt ttaaaaatat    960
ttacgtctta caggagctgg ataatccagg tgcaaaacga attctagagc ttgaccagtt    1020
taaggggcag caggacaaa aacgtttcca agacatgatg ggccacggat ctgactactc     1080
actcagtgaa gtgctgtggg tctgtgccaa cctctttagt gatgtccaat tcaagatgag    1140
tcataagagg atcatgctgt tcaccaatga agacaacccc catggcaatg acagtgccaa    1200
agccagccgg gccaggacca aagccggtga tctccgagat acaggcatct tccttgactt    1260
gatgcacctg aagaaacctg ggggcttga catatccttg ttctacagag atatcatcag     1320
catagcagag gatgaggacc tcagggttca cttttgagga atccagcaag ctagaagacct   1380 gttgcggaag gttcgcgcca aggagaccag gaagcgagca ctcagcaggt taaagctgaa    1440
gctcaacaaa gatatagtga tctctgtggg catttataat ctggtccaga aggctctcaa    1500
gcctcctcca ataaagctct atcgggaaac aaatgaacca gtgaaaacca agacccggac    1560
ctttaataca agtacaggcg gtttgcttct gcctagcgat accaagaggt ctcagatcta    1620
tgggagtcgt cagattatac tggagaaaga ggaaacagaa gagctaaaac ggtttgatga    1680
tccaggtttg atgctcatgg gtttcaagcc gttggtactg ctgaagaaac accattacct    1740
gaggccctcc ctgttcgtgt acccagagga gtcgctggtg attgggagct caaccctgtt    1800
cagtgctctg ctcatcaagt gtctggagaa ggaggttgca gcattgtgca gatacacacc    1860
ccgcaggaac atccctcctt attttgtggc tttggtgcca caggaagaag agttggatga    1920
ccagaaaatt caggtgactc ctccaggctt ccagctggtc ttttttaccct tgctgatga    1980 taaaaggaag atgcccttta ctgaaaaaat catggcaact ccagagcagg tgggcaagat    2040
gaaggctatc gttgagaagc ttcgcttcac atacagaagt gacagctttg agaacccgt     2100 gctgcagcag cacttcagga acctggaggc cttggccttg gatttgatgg agccggaaca    2160
agcagtggac ctgacattgc ccaaggttga agcaatgaat aaaagactgg gctccttggt    2220
ggatgagttt aaggagcttg tttacccacc agattacaat cctgaaggga agttaccaa     2280 gagaaaacac gataatgaag gttctggaag caaaaggccc aaggtggagt attcagaaga    2340
ggagctgaag acccacatca gcaagggtac gctgggcaag ttcactgtgc ccatgctgaa    2400
agaggcctgc cgggcttacg ggctgaagag tggtctgaag aagcaggagc tgctggaagc    2460
```

-continued

| | |
|---|---|
| cctcaccaag cacttccagg actgaccaga ggccgcgcgt ccagctgccc ttccgcagtg | 2520 |
| tggccaggct gcctggcctt gtcctcagcc agttaaaatg tgtttctcct gagctaggaa | 2580 |
| gagtctaccc gacataagtc gagggacttt atgtttttga ggctttctgt tgccatggtg | 2640 |
| atggtgtagc cctcccactt tgctgttctt tactttactg cctgaataaa gagccctaag | 2700 |
| tttgtactaa aaaaaaaaaa aaaaaaaaaa aaaaaaaaaa aaa | 2743 |

<210> SEQ ID NO 7
<211> LENGTH: 2493
<212> TYPE: DNA
<213> ORGANISM: Homo sapiens

<400> SEQUENCE: 7

| | |
|---|---|
| cccgggcggg cggcgggag gctctcgact gggcgggaag gtgcgggaag gttcgcggcg | 60 |
| gcggggtcgg ggaggtgcaa aaggatgaaa agcccgtgga agcggagctg agcagatccg | 120 |
| agccgggctg gcggcagaga aaccgcaggg agagcctcac tgctgagcgc ccctcgacgg | 180 |
| cggagcggca gcagcctccg tggcctccag catccgacaa gaagcttcag ccatgcaggc | 240 |
| cccacgggag ctcgcggtgg gcatcgacct gggcaccacc tactcgtgcg tgggcgtgtt | 300 |
| tcagcagggc cgcgtggaga tcctggccaa cgaccagggc aaccgcacca cgcccagcta | 360 |
| cgtggccttc accgacaccg agcggctggt cggggacgcg gccaagagcc aggcggccct | 420 |
| gaaccccac aacaccgtgt tcgatgccaa gcggctgatc gggcgcaagt tcgcggacac | 480 |
| cacggtgcag tcggacatga agcactggcc cttccaggtg gtgagcgagg gcggcaagcc | 540 |
| caaggtgcgc gtatgctacc gcggggagga caagacgttc taccccgagg agatctcgtc | 600 |
| catggtgctg agcaagatga aggagacggc cgaggcgtac ctgggccagc ccgtgaagca | 660 |
| cgcagtgatc accgtgccca cctatttcag taactcgcag cgccaggcca ccaaggacgc | 720 |
| gggggccatc gcggggctca aggtgctgcc gatcatcaat gaggccacgg cagcagccat | 780 |
| cgcctatggg ctggaccggc ggggcgcggg aaagcgcaac gtgctcattt ttgacctggg | 840 |
| tgggggcacc ttcgatgtgt cggttctctc cattgacgcc ggtgtctttg aggtgaaagc | 900 |
| cactgctgga gatacccacc tgggaggaga ggacttcgac aaccggctcg tgaaccactt | 960 |
| catggaagaa ttccggcgga agcatgggaa ggacctgagc gggaacaagc gtgccctgcg | 1020 |
| caggctgcgc acagcctgtg agcgcgccaa gcgcaccccg tcctccagca cccaggccac | 1080 |
| cctggagata gactccctgt tcgagggcgt ggacttctac aagtccatca ctcgtgcccg | 1140 |
| ctttgaggaa ctgtgctcag acctcttccg cagcaccctg agccggtgg agaaggccct | 1200 |
| gcgggatgcc aagctggaca aggcccagat tcatgacttc gtcctgggg gagggctcca | 1260 |
| ctcgcatccc caaggtgcag aagttgctgc aggacttctt caacggcaag gagctgaaca | 1320 |
| agagcatcaa ccctgatgag ctgtggcct atgggtctgc tgtgcaggcg gccgtgttga | 1380 |
| tggggacaa atgtgagaaa gtgcaggatc tcctgctgct ggatgtggct ccctgtctc | 1440 |
| tggggctgga gacagcaggt gggtgatga ccacgctgat ccagaggaac gccactatcc | 1500 |
| ccaccaagca gacccagact ttcaccacct actcggacaa ccagcctggg gtcttcatcc | 1560 |
| aggtgtatga ggttgagagg gccatgacca ggacaacaa cctgctgggg cgttttgaac | 1620 |
| tcattggcat ccctcctgcc ccacatggag tcccccagat agaggtgacg tttgacattg | 1680 |
| atgctaatgg catcctgagc gtgacagcca ctgacaggag cacaggtaag gctaacaaga | 1740 |
| tcaccaatga caagggccgg ctgagcaagg aggaggtgga gaggatggtt catgaagccg | 1800 |
| agcagtacgg ggctgaggat gaggcccaga gggacagagt ggctgccaaa aactcgctgg | 1860 |

```
aggcccatgt cttccatgtg aaaggttctt tgcaagagga aagccttagg gacaagattc   1920
ccgaagagga caggcgcaaa gtgcaagaca agtgtcagga agtccttgcc tggctggagc   1980
acaaccagct ggcagagaag gaggagtatg agcatcagaa gagggagctg agcaaatct    2040 gtcgcccat cttctccagg ctctatgggg ggcctggtgt ccctgggggc agcagttgta    2100
gcgctcaagc ccaccagggg gaccccagca ccggccccat cattgaggag gttgattgaa   2160
tggcccttcg tgataagtca gctgtgactg tcagggctat gctatgggcc ttctagactg   2220
tcttctatga tcctgccctt cagagatgaa gggcttgggg gggtcttccc tccaaagcta   2280
gaactttctt tccaggataa ctgaagtctt ttgactttt  gggggaggg cggttcatcc    2340 tcttctgctt caaataaaaa gtcattaatt tattaaaact tgtgtggcac tttaacattg   2400
ctttcaccta tattttgtgt attttgttac ttgtatgtat gaattttgtt atgtaaaata   2460
tagttataga cctaaataaa cttttaaaac tcc                                2493
```

<210> SEQ ID NO 8
<211> LENGTH: 643
<212> TYPE: PRT
<213> ORGANISM: Homo sapiens

<400> SEQUENCE: 8

```
Met Gln Ala Pro Arg Glu Leu Ala Val Gly Ile Asp Leu Gly Thr Thr
  1               5                  10                  15

Tyr Ser Cys Val Gly Val Phe Gln Gln Gly Arg Val Glu Ile Leu Ala
                 20                  25                  30

Asn Asp Gln Gly Asn Arg Thr Thr Pro Ser Tyr Val Ala Phe Thr Asp
             35                  40                  45

Thr Glu Arg Leu Val Gly Asp Ala Ala Lys Ser Gln Ala Ala Leu Asn
         50                  55                  60

Pro His Asn Thr Val Phe Asp Ala Lys Arg Leu Ile Gly Arg Lys Phe
     65                  70                  75                  80

Ala Asp Thr Thr Val Gln Ser Asp Met Lys His Trp Pro Phe Arg Val
                 85                  90                  95

Val Ser Glu Gly Gly Lys Pro Lys Val Arg Val Cys Tyr Arg Gly Glu
                100                 105                 110

Asp Lys Thr Phe Tyr Pro Glu Glu Ile Ser Ser Met Val Leu Ser Lys
            115                 120                 125

Met Lys Glu Thr Ala Glu Ala Tyr Leu Gly Gln Pro Val Lys His Ala
        130                 135                 140

Val Ile Thr Val Pro Ala Tyr Phe Asn Asp Ser Gln Arg Gln Ala Thr
145                 150                 155                 160

Lys Asp Ala Gly Ala Ile Ala Gly Leu Asn Val Leu Arg Ile Ile Asn
                165                 170                 175

Glu Pro Thr Ala Ala Ala Ile Ala Tyr Gly Leu Asp Arg Arg Gly Ala
            180                 185                 190

Gly Glu Arg Asn Val Leu Ile Phe Asp Leu Gly Gly Gly Thr Phe Asp
        195                 200                 205

Val Ser Val Leu Ser Ile Asp Ala Gly Val Phe Glu Val Lys Ala Thr
    210                 215                 220

Ala Gly Asp Thr His Leu Gly Gly Glu Asp Phe Asp Asn Arg Leu Val
225                 230                 235                 240

Asn His Phe Met Glu Glu Phe Arg Arg Lys His Gly Lys Asp Leu Ser
                245                 250                 255
```

-continued

Gly Asn Lys Arg Ala Leu Arg Arg Leu Arg Thr Ala Cys Glu Arg Ala
                260                 265                 270

Lys Arg Thr Leu Ser Ser Thr Gln Ala Thr Leu Glu Ile Asp Ser
        275                 280                 285

Leu Phe Glu Gly Val Asp Phe Tyr Thr Ser Ile Thr Arg Ala Arg Phe
        290                 295                 300

Glu Glu Leu Cys Ser Asp Leu Phe Arg Ser Thr Leu Glu Pro Val Glu
305                 310                 315                 320

Lys Ala Leu Arg Asp Ala Lys Leu Asp Lys Ala Gln Ile His Asp Val
                325                 330                 335

Val Leu Val Gly Gly Ser Thr Arg Ile Pro Lys Val Gln Lys Leu Leu
                340                 345                 350

Gln Asp Phe Phe Asn Gly Lys Glu Leu Asn Lys Ser Ile Asn Pro Asp
                355                 360                 365

Glu Ala Val Ala Tyr Gly Ala Ala Val Gln Ala Val Leu Met Gly
        370                 375                 380

Asp Lys Cys Glu Lys Val Gln Asp Leu Leu Leu Leu Asp Val Ala Pro
385                 390                 395                 400

Leu Ser Leu Gly Leu Glu Thr Ala Gly Gly Val Met Thr Thr Leu Ile
                405                 410                 415

Gln Arg Asn Ala Thr Ile Pro Thr Lys Gln Thr Gln Thr Phe Thr Thr
                420                 425                 430

Tyr Ser Asp Asn Gln Pro Gly Val Phe Ile Gln Val Tyr Glu Gly Glu
                435                 440                 445

Arg Ala Met Thr Lys Asp Asn Asn Leu Leu Gly Arg Phe Glu Leu Ser
450                 455                 460

Gly Ile Pro Pro Ala Pro Arg Gly Val Pro Gln Ile Glu Val Thr Phe
465                 470                 475                 480

Asp Ile Asp Ala Asn Gly Ile Leu Ser Val Thr Ala Thr Asp Arg Ser
                485                 490                 495

Thr Gly Lys Ala Asn Lys Ile Thr Ile Thr Asn Asp Lys Gly Arg Leu
                500                 505                 510

Ser Lys Glu Glu Val Glu Arg Met Val His Glu Ala Gln Tyr Lys
        515                 520                 525

Ala Glu Asp Glu Ala Gln Arg Asp Arg Val Ala Ala Lys Asn Ser Leu
530                 535                 540

Glu Ala His Val Phe His Val Lys Gly Ser Leu Gln Glu Glu Ser Leu
545                 550                 555                 560

Arg Asp Lys Ile Pro Glu Asp Arg Arg Lys Met Gln Asp Lys Cys
                565                 570                 575

Arg Glu Val Leu Ala Trp Leu Glu His Asn Gln Leu Ala Glu Lys Glu
        580                 585                 590

Glu Tyr Glu His Gln Lys Arg Glu Leu Glu Gln Ile Cys Arg Pro Ile
        595                 600                 605

Phe Ser Arg Leu Tyr Gly Gly Pro Gly Val Pro Gly Gly Ser Ser Cys
        610                 615                 620

Gly Thr Gln Ala Arg Gln Gly Asp Pro Ser Thr Gly Pro Ile Ile Glu
625                 630                 635                 640

Glu Val Asp

<210> SEQ ID NO 9
<211> LENGTH: 968
<212> TYPE: DNA
<213> ORGANISM: Homo sapiens

<400> SEQUENCE: 9

```
cccgggcggg cgggcgggag gctctcgact gggcgggaag gtgcgggaag gttcgcggcg      60
gcggggtcgg ggaggtgcaa aaggatgaaa agcccgtgga cggagctgag cagatccggc     120
cgggctggcg gcagagaaac cgcagggaga gcctcactgc tgagcgcccc tcgacgcggg     180
cggcagcagc ctccgtggcc tccagcatcc gacaagaagc ttcagccatg caggccccac     240
gggagctcgc ggtgggcatc gacctaggca ccacctactc gtgcgtgggc gtctttcagc     300
agggacgcgt ggagatccta gccaacgacc aaggcaaccg caccacgccc agctacgtgg     360
ccttcaccga caccgagcgg ctggtcgggg acgcggccaa gaaccaggcg ccctgaacc      420
cccacaacac cgtgttcgat gccaagcggc tgatcgggcg caagttcgcg gacaccacgg     480
tgcagtcgga tatgaagcac tggcccttca aggtggtgag cggaggcggc aagcccaagg     540
tgcgcgtatg ctaccgcggg gaggacaaga cgttctaccc cgaggagatc tcgtccatgg     600
tgctgaccaa gatgaaggag acggccgagg cgtaccttgg ccagcccgtg aagcacgcag     660
tgatcaccgt gcccacctat ttcagtaact cgcagcgcca agccaccaag gacgcggggg     720
ccatcgcggg gctcaaggtg ctgccgatca tcaatgaggc cacggcagca gccatcgcct     780
atgggctgga ccggcggcgc gcgggaaagc gcaacgtgct catttttgac ttgggtgggg     840
gcaccttcga tgtgtcggtt ctcaccattg acgccggtgt ctttgaggtg aaagccactg     900
ctggagatac ccacttggga ggagaggact cgacaaccg gctcgtgaac cacttcatgg      960
aagaattc                                                             968
```

<210> SEQ ID NO 10
<211> LENGTH: 223
<212> TYPE: PRT
<213> ORGANISM: Haemophilus ducreyi

<400> SEQUENCE: 10

```
Met Lys Lys Phe Leu Pro Ser Leu Leu Leu Met Gly Ser Val Ala Cys
  1               5                  10                  15

Ser Ser Asn Gln Arg Met Asn Asp Tyr Ser Gln Pro Glu Ser Gln Ser
             20                  25                  30

Asp Leu Ala Pro Lys Ser Ser Thr Ile Gln Pro Gln Pro Gln Pro Leu
         35                  40                  45

Leu Ser Lys Thr Pro Ser Met Ser Leu Asn Leu Ser Ser Ser Gly
     50                  55                  60

Pro Asn Arg Gln Val Leu Pro Ser Glu Pro Ser Asn Phe Met Thr Leu
 65                  70                  75                  80

Met Gly Gln Asn Gly Ala Leu Leu Thr Val Trp Ala Leu Ala Lys Arg
                 85                  90                  95

Asn Trp Leu Trp Ala Tyr Pro Asn Ile Tyr Ser Gln Asp Phe Gly Asn
            100                 105                 110

Ile Arg Asn Trp Lys Met Glu Pro Gly Lys His Arg Glu Tyr Phe Arg
        115                 120                 125

Phe Val Asn Gln Ser Leu Gly Thr Cys Val Glu Ala Tyr Gly Asn Gly
    130                 135                 140

Leu Ile His Asp Ile Cys Ser Leu Asp Lys Leu Ala Gln Glu Phe Glu
145                 150                 155                 160

Leu Leu Pro Thr Asp Ser Gly Ala Val Val Ile Lys Ser Val Ser Gln
                165                 170                 175

Gly Arg Cys Val Thr Tyr Asn Pro Val Ser Thr Thr Phe Tyr Ser Thr
```

```
                180             185             190
Val Thr Leu Ser Val Cys Asp Gly Ala Thr Glu Pro Ser Arg Asp Gln
            195             200             205
Thr Trp Tyr Leu Ala Pro Pro Val Leu Glu Ala Thr Ala Val Asn
        210             215             220

<210> SEQ ID NO 11
<211> LENGTH: 283
<212> TYPE: PRT
<213> ORGANISM: Haemophilus ducreyi

<400> SEQUENCE: 11

Met Gln Trp Val Lys Gln Leu Ser Val Val Phe Cys Val Met Leu Phe
  1               5                  10                  15
Ser Phe Ser Ser Tyr Ala Asn Leu Ser Asp Phe Lys Val Ala Thr Trp
                20                  25                  30
Asn Leu Gln Gly Ser Ser Ala Val Asn Glu Ser Lys Trp Asn Ile Asn
            35                  40                  45
Val Arg Gln Leu Leu Ser Gly Glu Gln Gly Ala Asp Ile Leu Met Val
        50                  55                  60
Gln Glu Ala Gly Ser Leu Pro Ser Ser Ala Val Arg Thr Ser Arg Val
 65                  70                  75                  80
Ile Gln His Gly Gly Thr Pro Ile Glu Glu Tyr Thr Trp Asn Leu Gly
                85                  90                  95
Thr Arg Ser Arg Pro Asn Met Val Tyr Ile Tyr Tyr Ser Arg Leu Asp
                100                 105                 110
Val Gly Ala Asn Arg Val Asn Leu Ala Ile Val Ser Arg Arg Gln Ala
            115                 120                 125
Asp Glu Ala Phe Ile Val His Ser Asp Ser Ser Val Leu Gln Ser Arg
        130                 135                 140
Pro Ala Val Gly Ile Arg Ile Gly Thr Asp Val Phe Phe Thr Val His
145                 150                 155                 160
Ala Leu Ala Thr Gly Gly Ser Asp Ala Val Ser Leu Ile Arg Asn Ile
                165                 170                 175
Phe Thr Thr Phe Asn Ser Ser Ser Pro Pro Glu Arg Arg Val Tyr
                180                 185                 190
Ser Trp Met Val Val Gly Asp Phe Asn Arg Ala Pro Ala Asn Leu Glu
            195                 200                 205
Val Ala Leu Arg Gln Glu Pro Ala Val Ser Glu Asn Thr Ile Ile Ile
        210                 215                 220
Ala Pro Thr Glu Pro Thr His Arg Ser Gly Asn Ile Leu Asp Tyr Ala
225                 230                 235                 240
Ile Leu His Asp Ala His Leu Pro Arg Arg Glu Gln Ala Arg Glu Arg
                245                 250                 255
Ile Gly Ala Ser Leu Met Leu Asn Gln Leu Arg Ser Gln Ile Thr Ser
            260                 265                 270
Asp His Phe Pro Val Ser Phe Val Arg Asp Arg
        275                 280

<210> SEQ ID NO 12
<211> LENGTH: 186
<212> TYPE: PRT
<213> ORGANISM: Haemophilus ducreyi

<400> SEQUENCE: 12

Met Lys Lys Tyr Leu Leu Ser Phe Leu Leu Ile Met Ile Leu Ala Leu
```

-continued

```
                1               5                  10                  15
Ala Ser His Ala Glu Ser Asn Pro Asp Pro Thr Thr Tyr Pro Asp Val
                20                  25                  30

Glu Leu Ser Pro Pro Arg Ile Ser Leu Arg Ser Leu Leu Thr Ala
            35                  40                  45

Gln Pro Val Lys Asn Asp His Tyr Asp Ser His Asn Tyr Leu Ser Thr
        50                  55                  60

His Trp Glu Leu Ile Asp Tyr Lys Gly Lys Glu Tyr Glu Lys Leu Arg
 65                  70                  75                  80

Asp Gly Gly Thr Leu Val Gln Phe Lys Val Val Gly Ala Ala Lys Cys
                85                  90                  95

Phe Ala Phe Leu Gly Lys Gly Thr Thr Asp Cys Lys Asp Thr Asp His
                100                 105                 110

Thr Val Phe Asn Leu Ile Pro Thr Asn Thr Gly Ala Phe Leu Ile Lys
            115                 120                 125

Asp Ala Leu Leu Gly Phe Cys Ile Thr Ser His Asp Phe Asp Asp Leu
130                 135                 140

Lys Leu Glu Pro Cys Gly Gly Ser Val Ser Gly Arg Thr Phe Ser Leu
145                 150                 155                 160

Ala Tyr Gln Trp Gly Ile Leu Pro Pro Phe Gly Pro Ser Lys Ile Leu
                165                 170                 175

Ile Pro Pro Val Arg Arg Asn Gln Gly Ser
            180                 185
```

<210> SEQ ID NO 13
<211> LENGTH: 268
<212> TYPE: PRT
<213> ORGANISM: Campylobacter jejuni

<400> SEQUENCE: 13

```
Met Gln Lys Ile Ile Val Phe Ile Leu Cys Cys Phe Met Thr Phe Phe
 1               5                  10                  15

Leu Tyr Ala Cys Ser Ser Lys Phe Glu Asn Val Asn Pro Leu Gly Arg
                20                  25                  30

Ser Phe Gly Glu Phe Glu Asp Thr Asp Pro Leu Lys Leu Gly Leu Glu
            35                  40                  45

Pro Thr Phe Pro Thr Asn Gln Glu Ile Pro Ser Leu Ile Ser Gly Ala
        50                  55                  60

Asp Leu Val Pro Ile Thr Pro Ile Thr Pro Pro Leu Thr Arg Thr Ser
 65                  70                  75                  80

Asn Ser Ala Asn Asn Ala Ala Asn Gly Ile Asn Pro Arg Phe Lys
                85                  90                  95

Asp Glu Ala Phe Asn Asp Val Leu Ile Phe Glu Asn Arg Pro Ala Val
                100                 105                 110

Ser Asp Phe Leu Thr Ile Leu Gly Pro Ser Gly Ala Ala Leu Thr Val
            115                 120                 125

Trp Ala Leu Ala Gln Gly Asn Trp Ile Trp Gly Tyr Thr Leu Ile Asp
130                 135                 140

Ser Lys Gly Phe Gly Asp Ala Arg Val Trp Gln Leu Leu Tyr Pro
145                 150                 155                 160

Asn Asp Phe Ala Met Ile Lys Asn Ala Lys Thr Asn Thr Cys Leu Asn
                165                 170                 175

Ala Tyr Gly Asn Gly Ile Val His Tyr Pro Cys Asp Ala Ser Asn His
                180                 185                 190
```

```
Ala Gln Met Trp Lys Leu Ile Pro Met Ser Asn Thr Ala Val Gln Ile
            195                 200                 205

Lys Asn Leu Gly Asn Gly Lys Cys Ile Gln Ala Pro Ile Thr Asn Leu
    210                 215                 220

Tyr Gly Asp Phe His Lys Val Phe Lys Ile Phe Thr Val Glu Cys Ala
225                 230                 235                 240

Lys Lys Asp Asn Phe Asp Gln Gln Trp Phe Leu Thr Thr Pro Pro Phe
                245                 250                 255

Thr Ala Lys Pro Leu Tyr Arg Gln Gly Glu Val Arg
            260                 265

<210> SEQ ID NO 14
<211> LENGTH: 265
<212> TYPE: PRT
<213> ORGANISM: Campylobacter jejuni

<400> SEQUENCE: 14

Met Lys Lys Ile Ile Cys Leu Phe Leu Ser Phe Asn Leu Ala Phe Ala
 1               5                  10                  15

Asn Leu Glu Asn Phe Asn Val Gly Thr Trp Asn Leu Gln Gly Ser Ser
            20                  25                  30

Ala Ala Thr Glu Ser Lys Trp Ser Val Ser Val Arg Gln Leu Val Ser
        35                  40                  45

Gly Ala Asn Pro Leu Asp Ile Leu Met Ile Gln Glu Ala Gly Thr Leu
    50                  55                  60

Pro Arg Thr Ala Thr Pro Thr Gly Arg His Val Gln Gln Gly Gly Thr
65                  70                  75                  80

Pro Ile Asp Glu Tyr Glu Trp Asn Leu Gly Thr Leu Ser Arg Pro Asp
                85                  90                  95

Arg Val Phe Ile Tyr Tyr Ser Arg Val Asp Val Gly Ala Asn Arg Val
            100                 105                 110

Asn Leu Ala Ile Val Ser Arg Met Gln Ala Glu Val Ile Val Leu
        115                 120                 125

Pro Pro Pro Thr Thr Val Ser Arg Pro Ile Ile Gly Ile Arg Asn Gly
    130                 135                 140

Asn Asp Ala Phe Phe Asn Ile His Ala Leu Ala Asn Gly Gly Thr Asp
145                 150                 155                 160

Val Gly Ala Ile Ile Thr Ala Val Asp Ala His Phe Ala Asn Met Pro
                165                 170                 175

Gln Val Asn Trp Met Ile Ala Gly Asp Phe Asn Arg Asp Pro Ser Thr
            180                 185                 190

Ile Thr Ser Thr Val Asp Arg Glu Leu Ala Asn Arg Ile Arg Val Val
        195                 200                 205

Phe Pro Thr Ser Ala Thr Gln Ala Ser Gly Gly Thr Leu Asp Tyr Ala
    210                 215                 220

Ile Thr Gly Asn Ser Asn Arg Gln Gln Thr Tyr Thr Pro Pro Leu Leu
225                 230                 235                 240

Ala Ala Ile Leu Met Leu Ala Ser Leu Arg Ser His Ile Val Ser Asp
                245                 250                 255

His Phe Pro Val Asn Phe Arg Lys Phe
            260                 265

<210> SEQ ID NO 15
<211> LENGTH: 189
<212> TYPE: PRT
<213> ORGANISM: Campylobacter jejuni
```

```
<400> SEQUENCE: 15

Met Lys Lys Ile Ile Thr Leu Phe Phe Met Phe Ile Thr Leu Ala Phe
1               5                   10                  15

Ala Thr Pro Thr Gly Asp Leu Lys Asp Phe Thr Glu Met Val Ser Ile
            20                  25                  30

Arg Ser Leu Glu Thr Gly Ile Phe Leu Ser Ala Phe Arg Asp Thr Ser
        35                  40                  45

Lys Asp Pro Ile Asp Gln Asn Trp Asn Ile Lys Glu Ile Val Leu Ser
50                  55                  60

Asp Glu Leu Lys Gln Lys Asp Lys Leu Ala Asp Glu Leu Pro Phe Gly
65                  70                  75                  80

Tyr Val Gln Phe Thr Asn Pro Lys Glu Ser Asp Leu Cys Leu Ala Ile
                85                  90                  95

Leu Glu Asp Gly Thr Phe Gly Ala Lys Ser Cys Gln Asp Asp Leu Lys
            100                 105                 110

Asp Gly Lys Leu Glu Thr Val Phe Ser Ile Met Pro Thr Thr Thr Ser
        115                 120                 125

Ala Val Gln Ile Arg Ser Leu Val Leu Glu Ser Asp Glu Cys Ile Val
    130                 135                 140

Thr Phe Phe Asn Pro Asn Ile Pro Ile Gln Lys Arg Phe Gly Ile Ala
145                 150                 155                 160

Pro Cys Thr Leu Asp Pro Ile Phe Phe Ala Glu Val Asn Glu Leu Met
                165                 170                 175

Ile Ile Thr Pro Pro Leu Thr Ala Ala Thr Pro Leu Glu
                180                 185

<210> SEQ ID NO 16
<211> LENGTH: 33
<212> TYPE: PRT
<213> ORGANISM: Campylobacter jejuni

<400> SEQUENCE: 16

Met Leu Thr Trp Gln Gln Ile Tyr Asp Pro Phe Ser Asn Ile Trp Leu
1               5                   10                  15

Ser Ala Leu Val Ala Phe Leu Pro Ile Leu Cys Phe Leu Val Cys Leu
            20                  25                  30

Val

<210> SEQ ID NO 17
<211> LENGTH: 237
<212> TYPE: PRT
<213> ORGANISM: Escherichia coli

<400> SEQUENCE: 17

Met Asp Lys Lys Leu Ile Ala Phe Leu Cys Thr Leu Ile Ile Thr Gly
1               5                   10                  15

Cys Ser Asn Gly Ile Gly Asp Ser Pro Ser Pro Gly Lys Asn Val
            20                  25                  30

Glu Leu Val Gly Ile Pro Gly Gln Gly Ile Ala Val Thr Ser Asn Gly
        35                  40                  45

Ala Thr Pro Thr Leu Gly Ala Asn Asn Thr Glu Phe Pro Glu Val Ser
50                  55                  60

Ile Met Ser Thr Gly Gly Ala Leu Leu Thr Ile Trp Ala Arg Pro Val
65                  70                  75                  80

Arg Asn Trp Leu Trp Gly Tyr Thr Pro Phe Asp Ser Val Asn Phe Gly
```

```
                85                  90                  95
Glu Asn Arg Asn Trp Lys Val Val Asp Gly Lys Asp Ala Gly Thr Val
            100                 105                 110
Lys Phe Val Asn Val Ala Gln Gly Thr Cys Met Glu Ala Phe Lys Asn
        115                 120                 125
Gly Val Ile His Asn Thr Cys Asp Asp Asn Ser Leu Ser Gln Glu Phe
    130                 135                 140
Gln Leu Leu Pro Ser Thr Asn Gly Asn Val Leu Ile Arg Ser Ser Ala
145                 150                 155                 160
Leu Gln Thr Cys Ile Arg Ala Asp Tyr Leu Ser Arg Thr Ile Leu Ser
                165                 170                 175
Pro Phe Ala Phe Thr Ile Thr Leu Glu Lys Cys Pro Gly Ala Lys Glu
            180                 185                 190
Glu Thr Gln Glu Met Leu Trp Ala Ile Ser Pro Pro Val Arg Ala Ala
        195                 200                 205
Lys Pro Asn Leu Ile Lys Pro Glu Leu Arg Pro Phe Arg Pro Leu Pro
    210                 215                 220
Ile Pro Pro His Asp Lys Pro Asp Gly Met Glu Gly Val
225                 230                 235

<210> SEQ ID NO 18
<211> LENGTH: 273
<212> TYPE: PRT
<213> ORGANISM: Escherichia coli

<400> SEQUENCE: 18

Met Lys Lys Leu Leu Phe Leu Leu Met Ile Leu Pro Gly Ile Ser Phe
  1               5                  10                  15
Ala Asp Leu Ser Asp Phe Lys Val Ala Thr Trp Asn Leu Gln Gly Ser
                20                  25                  30
Asn Ala Pro Thr Glu Asn Lys Trp Asn Thr His Val Arg Gln Leu Val
            35                  40                  45
Thr Gly Ser Gly Ala Val Asp Ile Leu Met Val Gln Glu Ala Gly Ala
    50                  55                  60
Val Pro Ala Ser Ala Thr Leu Thr Glu Arg Glu Phe Ser Thr Pro Gly
65                  70                  75                  80
Ile Pro Met Asn Glu Tyr Ile Trp Asn Thr Gly Thr Asn Ser Arg Pro
                85                  90                  95
Gln Glu Leu Phe Ile Tyr Phe Ser Arg Val Asp Ala Phe Ala Asn Arg
            100                 105                 110
Val Asn Leu Ala Ile Val Ser Asn Arg Arg Ala Asp Glu Val Ile Val
        115                 120                 125
Leu Pro Pro Pro Thr Val Val Ser Arg Pro Ile Ile Gly Ile Arg Ile
    130                 135                 140
Gly Asn Asp Val Phe Phe Ser Thr His Ala Leu Ala Asn Arg Gly Val
145                 150                 155                 160
Asp Ser Gly Ala Ile Val Asn Ser Val Phe Glu Phe Asn Arg Gln
                165                 170                 175
Thr Asp Pro Ile Arg Gln Ala Ala Asn Trp Met Ile Ala Gly Asp Phe
            180                 185                 190
Asn Arg Ser Pro Ala Thr Leu Phe Ser Thr Leu Glu Pro Gly Ile Arg
        195                 200                 205
Asn His Val Asn Ile Ile Ala Pro Pro Asp Pro Thr Gln Ala Ser Gly
    210                 215                 220
```

```
Gly Val Leu Asp Tyr Ala Val Val Gly Asn Ser Val Ser Phe Val Leu
225                 230                 235                 240

Pro Leu Leu Arg Ala Ser Leu Leu Phe Gly Leu Arg Gly Gln Ile
            245                 250                 255

Ala Ser Asp His Phe Pro Val Gly Phe Ile Pro Gly Arg Gly Ala Arg
            260                 265                 270

Arg

<210> SEQ ID NO 19
<211> LENGTH: 190
<212> TYPE: PRT
<213> ORGANISM: Escherichia coli

<400> SEQUENCE: 19

Met Lys Thr Val Ile Val Phe Phe Val Leu Leu Thr Gly Cys Ala
 1               5                  10                  15

Ser Glu Pro Ala Asn Gln Arg Asn Leu Leu Thr Gln Phe Val Gly Asn
                20                  25                  30

Asn Ala Pro Val Asp Pro Glu Pro Ser Pro Val Leu Val Asn Ile Arg
            35                  40                  45

Asn Val Leu Thr Gly Gly Ile Ile Arg Asn Pro Val Gly Ser Asp Phe
        50                  55                  60

Asn Val Asn Asn Trp Val Ile Ser Glu Val Lys Thr Asn Asp Leu Asp
 65                 70                  75                  80

Leu Ile Ser Ala Pro Gly Gly His Val Gln Ile Lys Asn Pro Asp Gly
                85                  90                  95

Asn Glu Cys Phe Ala Ile Leu Asn Gly Gln Leu Ala Val Ala Lys Gln
            100                 105                 110

Cys Ser Glu Ser Asp Arg Asn Ala Leu Phe Thr Phe Ile Thr Ser Asp
        115                 120                 125

Thr Gly Ala Val Gln Ile Lys Ser Ile Gly Ser Gly Gln Cys Leu Gly
    130                 135                 140

Asn Gly Glu Ser Ile Thr Asp Phe Arg Leu Lys Lys Cys Val Asp Asp
145                 150                 155                 160

Leu Gly Arg Pro Phe Asp Thr Val Pro Pro Gly Leu Leu Trp Met Leu
                165                 170                 175

Asn Pro Pro Leu Ser Pro Ala Ile Met Ser Pro Leu Thr Ser
            180                 185                 190

<210> SEQ ID NO 20
<211> LENGTH: 258
<212> TYPE: PRT
<213> ORGANISM: Escherichia coli

<400> SEQUENCE: 20

Met Ala Asn Lys Arg Thr Pro Ile Phe Ile Ala Gly Ile Leu Ile Pro
 1               5                  10                  15

Ile Leu Leu Asn Gly Cys Ser Ser Gly Lys Asn Lys Ala Tyr Leu Asp
                20                  25                  30

Pro Lys Val Phe Pro Pro Gln Val Glu Gly Gly Pro Thr Val Pro Ser
            35                  40                  45

Pro Asp Glu Pro Gly Leu Pro Leu Pro Gly Pro Ala Leu Pro
        50                  55                  60

Thr Asn Gly Ala Ile Pro Ile Pro Glu Pro Gly Thr Ala Pro Ala Val
 65                 70                  75                  80

Ser Leu Met Asn Met Asp Gly Ser Val Leu Thr Met Trp Ser Arg Gly
```

-continued

```
                85                  90                  95
Ala Gly Ser Ser Leu Trp Ala Tyr Tyr Ile Gly Asp Ser Asn Ser Phe
            100                 105                 110

Gly Glu Leu Arg Asn Trp Gln Ile Met Pro Gly Thr Arg Pro Asn Thr
        115                 120                 125

Ile Gln Phe Arg Asn Val Asp Val Gly Thr Cys Met Thr Ser Phe Pro
    130                 135                 140

Gly Phe Lys Gly Gly Val Gln Leu Ser Thr Ala Pro Cys Lys Phe Gly
145                 150                 155                 160

Pro Glu Arg Phe Asp Phe Gln Pro Met Ala Thr Arg Asn Gly Asn Tyr
                165                 170                 175

Gln Leu Lys Ser Leu Ser Thr Gly Leu Cys Ile Arg Ala Asn Phe Leu
            180                 185                 190

Gly Arg Thr Pro Ser Ser Pro Tyr Ala Thr Thr Leu Thr Met Glu Arg
        195                 200                 205

Cys Pro Ser Ser Gly Glu Lys Asn Phe Glu Phe Met Trp Ser Ile Ser
    210                 215                 220

Glu Pro Leu Arg Pro Ala Leu Ala Thr Ile Ala Lys Pro Glu Ile Arg
225                 230                 235                 240

Pro Phe Pro Pro Gln Pro Ile Glu Pro Asp Glu His Ser Thr Gly Gly
                245                 250                 255

Glu Gln

<210> SEQ ID NO 21
<211> LENGTH: 269
<212> TYPE: PRT
<213> ORGANISM: Escherichia coli

<400> SEQUENCE: 21

Met Lys Lys Tyr Ile Ile Ser Leu Ile Val Phe Leu Ser Phe Tyr Ala
  1               5                  10                  15

Gln Ala Asp Leu Thr Asp Phe Arg Val Ala Thr Trp Asn Leu Gln Gly
                20                  25                  30

Ala Ser Ala Thr Thr Glu Ser Lys Trp Asn Ile Asn Val Arg Gln Leu
            35                  40                  45

Ile Ser Gly Glu Asn Ala Val Asp Ile Leu Ala Val Gln Glu Ala Gly
        50                  55                  60

Ser Pro Pro Ser Thr Ala Val Asp Thr Gly Thr Leu Ile Pro Ser Pro
 65                 70                  75                  80

Gly Ile Pro Val Arg Glu Leu Ile Trp Asn Leu Ser Thr Asn Ser Arg
                85                  90                  95

Pro Gln Gln Val Tyr Ile Tyr Phe Ser Ala Val Asp Ala Leu Gly Gly
            100                 105                 110

Arg Val Asn Leu Ala Leu Val Ser Asn Arg Arg Ala Asp Glu Val Phe
        115                 120                 125

Val Leu Ser Pro Val Arg Gln Gly Gly Arg Pro Leu Leu Gly Ile Arg
    130                 135                 140

Ile Gly Asn Asp Ala Phe Phe Thr Ala His Ala Ile Ala Met Arg Asn
145                 150                 155                 160

Asn Asp Ala Pro Ala Leu Val Glu Glu Val Tyr Asn Phe Phe Arg Asp
                165                 170                 175

Ser Arg Asp Pro Val His Gln Ala Leu Asn Trp Met Ile Leu Gly Asp
            180                 185                 190

Phe Asn Arg Glu Pro Ala Asp Leu Glu Met Asn Leu Thr Val Pro Val
```

-continued

```
               195                 200                 205
Arg Arg Ala Ser Glu Ile Ile Ser Pro Ala Ala Thr Gln Thr Ser
    210                 215                 220

Gln Arg Thr Leu Asp Tyr Ala Val Ala Gly Asn Ser Val Ala Phe Arg
225                 230                 235                 240

Pro Ser Pro Leu Gln Ala Gly Ile Val Tyr Gly Ala Arg Arg Thr Gln
                245                 250                 255

Ile Ser Ser Asp His Phe Pro Val Gly Val Ser Arg Arg
            260                 265
```

<210> SEQ ID NO 22
<211> LENGTH: 181
<212> TYPE: PRT
<213> ORGANISM: Escherichia coli

<400> SEQUENCE: 22

```
Met Lys Lys Leu Ala Ile Val Phe Thr Met Leu Leu Ile Ala Gly Cys
1               5                   10                  15

Ser Ser Ser Gln Asp Ser Ala Asn Asn Gln Ile Asp Glu Leu Gly Lys
                20                  25                  30

Glu Asn Asn Ser Leu Phe Thr Phe Arg Asn Ile Gln Ser Gly Leu Met
            35                  40                  45

Ile His Asn Gly Leu His Gln His Gly Arg Glu Thr Ile Gly Trp Glu
        50                  55                  60

Ile Val Pro Val Lys Thr Pro Glu Glu Ala Leu Val Thr Asp Gln Ser
65                  70                  75                  80

Gly Trp Ile Met Ile Arg Thr Pro Asn Thr Asp Gln Cys Leu Gly Thr
                85                  90                  95

Pro Asp Gly Arg Asn Leu Leu Lys Met Thr Cys Asn Ser Thr Ala Lys
                100                 105                 110

Lys Thr Leu Phe Ser Leu Ile Pro Ser Thr Gly Ala Val Gln Ile
            115                 120                 125

Lys Ser Val Leu Ser Gly Leu Cys Phe Leu Asp Ser Lys Asn Ser Gly
        130                 135                 140

Leu Ser Phe Glu Thr Gly Lys Cys Ile Ala Asp Phe Lys Lys Pro Phe
145                 150                 155                 160

Glu Val Val Pro Gln Ser His Leu Trp Met Leu Asn Pro Leu Asn Thr
                165                 170                 175

Glu Ser Pro Ile Ile
            180
```

<210> SEQ ID NO 23
<211> LENGTH: 155
<212> TYPE: PRT
<213> ORGANISM: Escherichia coli

<400> SEQUENCE: 23

```
Glu Asn Lys Trp Asn Thr His Val Arg Gln Leu Val Thr Gly Ser Gly
1               5                   10                  15

Ala Val Asp Ile Leu Met Val Gln Glu Ala Gly Ala Val Pro Ala Ser
                20                  25                  30

Ala Thr Leu Thr Glu Arg Glu Phe Ser Thr Pro Gly Ile Pro Met Asn
            35                  40                  45

Glu Tyr Ile Trp Asn Thr Gly Thr Asn Ser Arg Pro Gln Glu Leu Phe
        50                  55                  60

Ile Tyr Phe Ser Arg Val Asp Ala Phe Ala Asn Arg Val Asn Leu Ala
```

```
            65                  70                  75                  80
Ile Val Ser Asn Arg Arg Ala Asp Glu Val Ile Val Leu Pro Pro Pro
                    85                  90                  95

Thr Val Val Ser Arg Pro Ile Ile Gly Ile Arg Ile Gly Asn Asp Val
                100                 105                 110

Phe Phe Ser Thr His Ala Leu Ala Asn Arg Gly Val Asp Ser Gly Ala
                115                 120                 125

Ile Val Asn Ser Val Phe Glu Phe Phe Asn Arg Gln Thr Asp Pro Ile
130                 135                 140

Arg Gln Ala Ala Asn Trp Met Ile Ala Gly Asp
145                 150                 155

<210> SEQ ID NO 24
<211> LENGTH: 609
<212> TYPE: PRT
<213> ORGANISM: Homo sapiens

<400> SEQUENCE: 24

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
                20                  25                  30

Ser Gly Arg Asp Ser Leu Ile Phe Leu Val Asp Ala Ser Lys Ala Met
            35                  40                  45

Phe Glu Ser Gln Ser Glu Asp Glu Leu Thr Pro Phe Asp Met Ser Ile
    50                  55                  60

Gln Cys Ile Gln Ser Val Tyr Ile Ser Lys Ile Ile Ser Ser Asp Arg
65                  70                  75                  80

Asp Leu Leu Ala Val Val Phe Tyr Gly Thr Glu Lys Asp Lys Asn Ser
                85                  90                  95

Val Asn Phe Lys Asn Ile Tyr Val Leu Gln Glu Leu Asp Asn Pro Gly
                100                 105                 110

Ala Lys Arg Ile Leu Glu Leu Asp Gln Phe Lys Gly Gln Gln Gly Gln
            115                 120                 125

Lys Arg Phe Gln Asp Met Met Gly His Gly Ser Asp Tyr Ser Leu Ser
130                 135                 140

Glu Val Leu Trp Val Cys Ala Asn Leu Phe Ser Asp Val Gln Phe Lys
145                 150                 155                 160

Met Ser His Lys Arg Ile Met Leu Phe Thr Asn Glu Asp Asn Pro His
                165                 170                 175

Gly Asn Asp Ser Ala Lys Ala Ser Arg Ala Arg Thr Lys Ala Gly Asp
                180                 185                 190

Leu Arg Asp Thr Gly Ile Phe Leu Asp Leu Met His Leu Lys Lys Pro
            195                 200                 205

Gly Gly Phe Asp Ile Ser Leu Phe Tyr Arg Asp Ile Ile Ser Ile Ala
            210                 215                 220

Glu Asp Glu Asp Leu Arg Val His Phe Glu Glu Ser Ser Lys Leu Glu
225                 230                 235                 240

Asp Leu Leu Arg Lys Val Arg Ala Lys Glu Thr Arg Lys Arg Ala Leu
                245                 250                 255

Ser Arg Leu Lys Leu Lys Leu Asn Lys Asp Ile Val Ile Ser Val Gly
            260                 265                 270

Ile Tyr Asn Leu Val Gln Lys Ala Leu Lys Pro Pro Pro Ile Lys Leu
        275                 280                 285
```

```
Tyr Arg Glu Thr Asn Glu Pro Val Lys Thr Lys Thr Arg Thr Phe Asn
        290                 295                 300
Thr Ser Thr Gly Gly Leu Leu Leu Pro Ser Asp Thr Lys Arg Ser Gln
305                 310                 315                 320
Ile Tyr Gly Ser Arg Gln Ile Ile Leu Glu Lys Glu Thr Glu Glu
            325                 330                 335
Leu Lys Arg Phe Asp Asp Pro Gly Leu Met Leu Met Gly Phe Lys Pro
        340                 345                 350
Leu Val Leu Leu Lys Lys His His Tyr Leu Arg Pro Ser Leu Phe Val
            355                 360                 365
Tyr Pro Glu Glu Ser Leu Val Ile Gly Ser Ser Thr Leu Phe Ser Ala
        370                 375                 380
Leu Leu Ile Lys Cys Leu Glu Lys Glu Val Ala Ala Leu Cys Arg Tyr
385                 390                 395                 400
Thr Pro Arg Arg Asn Ile Pro Pro Tyr Phe Ala Leu Val Pro Gln
            405                 410                 415
Glu Glu Glu Leu Asp Asp Gln Lys Ile Gln Val Thr Pro Pro Gly Phe
        420                 425                 430
Gln Leu Val Phe Leu Pro Phe Ala Asp Asp Lys Arg Lys Met Pro Phe
            435                 440                 445
Thr Glu Lys Ile Met Ala Thr Pro Glu Gln Val Gly Lys Met Lys Ala
450                 455                 460
Ile Val Glu Lys Leu Arg Phe Thr Tyr Arg Ser Asp Ser Phe Glu Asn
465                 470                 475                 480
Pro Val Leu Gln Gln His Phe Arg Asn Leu Glu Ala Leu Ala Leu Asp
            485                 490                 495
Leu Met Glu Pro Glu Gln Ala Val Asp Leu Thr Leu Pro Lys Val Glu
        500                 505                 510
Ala Met Asn Lys Arg Leu Gly Ser Leu Val Asp Glu Phe Lys Glu Leu
        515                 520                 525
Val Tyr Pro Pro Asp Tyr Asn Pro Glu Gly Lys Val Thr Lys Arg Lys
        530                 535                 540
His Asp Asn Glu Gly Ser Gly Ser Lys Arg Pro Lys Val Glu Tyr Ser
545                 550                 555                 560
Glu Glu Glu Leu Lys Thr His Ile Ser Lys Gly Thr Leu Gly Lys Phe
            565                 570                 575
Thr Val Pro Met Leu Lys Glu Ala Cys Arg Ala Tyr Gly Leu Lys Ser
            580                 585                 590
Gly Leu Lys Lys Gln Glu Leu Leu Glu Ala Leu Thr Lys His Phe Gln
        595                 600                 605
Asp

<210> SEQ ID NO 25
<211> LENGTH: 247
<212> TYPE: PRT
<213> ORGANISM: Homo sapiens

<400> SEQUENCE: 25

Met Gln Ala Pro Arg Glu Leu Ala Val Gly Ile Asp Leu Gly Thr Thr
1               5                   10                  15
Tyr Ser Cys Val Gly Val Phe Gln Gln Gly Arg Val Glu Ile Leu Ala
            20                  25                  30
Asn Asp Gln Gly Asn Arg Thr Thr Pro Ser Tyr Val Ala Phe Thr Asp
        35                  40                  45
```

-continued

```
Thr Glu Arg Leu Val Gly Asp Ala Ala Lys Asn Gln Ala Ala Leu Asn
    50                  55                  60
Pro His Asn Thr Val Phe Asp Ala Lys Arg Leu Ile Gly Arg Lys Phe
65                  70                  75                  80
Ala Asp Thr Thr Val Gln Ser Asp Met Lys His Trp Pro Phe Lys Val
                85                  90                  95
Val Ser Gly Gly Gly Lys Pro Lys Val Arg Val Cys Tyr Arg Gly Glu
            100                 105                 110
Asp Lys Thr Phe Tyr Pro Glu Glu Ile Ser Ser Met Val Leu Thr Lys
        115                 120                 125
Met Lys Glu Thr Ala Glu Ala Tyr Leu Gly Gln Pro Val Lys His Ala
    130                 135                 140
Val Ile Thr Val Pro Thr Tyr Phe Ser Asn Ser Gln Arg Gln Ala Thr
145                 150                 155                 160
Lys Asp Ala Gly Ala Ile Ala Gly Leu Lys Val Leu Pro Ile Ile Asn
            165                 170                 175
Glu Ala Thr Ala Ala Ile Ala Tyr Gly Leu Asp Arg Arg Arg Ala
            180                 185                 190
Gly Lys Arg Asn Val Leu Ile Phe Asp Leu Gly Gly Gly Thr Phe Asp
        195                 200                 205
Val Ser Val Leu Thr Ile Asp Ala Gly Val Phe Glu Val Lys Ala Thr
    210                 215                 220
Ala Gly Asp Thr His Leu Gly Gly Glu Asp Phe Asp Asn Arg Leu Val
225                 230                 235                 240
Asn His Phe Met Glu Glu Phe
                245
```